(12) United States Patent
Ellis et al.

(10) Patent No.: US 7,834,009 B2
(45) Date of Patent: Nov. 16, 2010

(54) 4-HYDROXY-5,6-DIHYDRO-1H-PYRIDIN-2-ONE COMPOUNDS

(75) Inventors: David Ellis, San Diego, CA (US);
Liansheng Li, San Diego, CA (US);
Chinh V. Tran, San Diego, CA (US);
Frank Ruebsam, San Diego, CA (US);
Yuefen Zhou, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 463 days.

(21) Appl. No.: 11/845,515

(22) Filed: Aug. 27, 2007

(65) Prior Publication Data

US 2009/0062263 A1    Mar. 5, 2009

(51) Int. Cl.
*C07D 417/04* (2006.01)
*A61K 31/549* (2006.01)

(52) U.S. Cl. .................. 514/223.2; 544/12; 544/13

(58) Field of Classification Search ............ 544/12, 544/13; 514/223.2
See application file for complete search history.

(56) References Cited

U.S. PATENT DOCUMENTS

| | | | |
|---|---|---|---|
| 7,582,626 B2 * | 9/2009 | Tran et al. ............. | 514/223.2 |
| 2005/0153877 A1 | 7/2005 | Miao et al. | |
| 2006/0040927 A1 | 2/2006 | Blake et al. | |
| 2006/0189602 A1 | 8/2006 | Zhou et al. | |
| 2006/0211695 A1 | 9/2006 | Borzilleri et al. | |
| 2006/0252785 A1 | 11/2006 | Blake et al. | |

FOREIGN PATENT DOCUMENTS

| | | |
|---|---|---|
| WO | WO-01/85172 A1 | 11/2001 |
| WO | WO-02/098424 A1 | 12/2002 |
| WO | WO-03/059356 A2 | 7/2003 |
| WO | WO-2006115221 | 11/2006 |

OTHER PUBLICATIONS

Vippagunta et al. "Crystalline Solids," Advanced Drug Delivery Reviews, 2001, 48, pp. 3-26.*
U.S. Appl. No. 11/766,668, Ellis et al.
U.S. Appl. No. 11/898,334, Zhou et al.
U.S. Appl. No. 11/861,678, Dragovich et al.
U.S. Appl. No. 11/955,144, Tran et al.
U.S. Appl. No. 11/955,193, Ruebsam et al.
U.S. Appl. No. 12/048,933, Ruebsam et al.
U.S. Appl. No. 12/061,499, Tran et al.
U.S. Appl. No. 11/845,515, Ellis et al.
Int'l Search Report of In'tl Appl. No. PCT/US05/45588.
Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).
Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1 H)-ones by Intramolecular Wittig Reaction. Molecules, Feb. 28, 2002, vol. 7, pp. 124-128.

* cited by examiner

*Primary Examiner*—Kahsay T Habte
(74) *Attorney, Agent, or Firm*—Connolly Bove Lodge & Hutz LLP

(57) ABSTRACT

The invention is directed to 4-hydroxy-5,6-dihydro-1H-pyridin-2-one compounds of Formula I and pharmaceutical compositions containing such compounds that are useful in treating infections by hepatitis C virus:

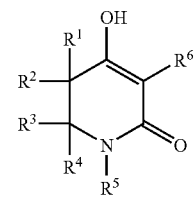

wherein $R^6$ is

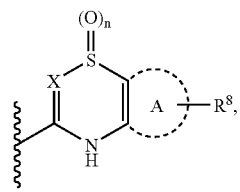

X is N,
Ring A is a 5- or 6-membered aryl, optionally substituted by 1-3 $R^8$ moieties,
n is 2, and
$R^1$-$R^6$ and $R^8$ are defined herein.

19 Claims, No Drawings

4-HYDROXY-5,6-DIHYDRO-1H-PYRIDIN-2-ONE COMPOUNDS

FIELD OF THE INVENTION

The invention is directed to 4-hydroxy-5,6-dihydro-1H-pyridin-2-one compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $31,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of recent publications have described NS5B inhibitors useful in the treatment of hepatitis C infection. See, e.g., U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 2002/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel 4-hydroxy-5,6-dihydro-1H-pyridin-2-one compounds and pharmaceutically acceptable salts thereof, which are useful in treating or preventing a hepatitis C virus infection in a patient in need thereof comprising administering to the patient a therapeutically or prophylactically effective amount of a 4-hydroxy-5,6-dihydro-1H-pyridin-2-one compound.

In a general aspect, the invention relates to compounds of Formula I

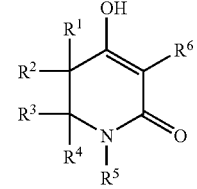

I wherein
$R^1$, $R^2$, $R^3$, and $R^4$ are independently H, halo, cyano, hydroxyl, $C_1$-$C_6$ hydroxyalkyl, $C_1$-$C_6$ alkoxy, amino, $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_2$-$C_6$ alkenyl, $C_2$-$C_6$ alkynyl, aryl, $C_1$-$C_6$ alkylene(aryl), heterocyclyl, or $C_1$-$C_6$ alkylene(heterocyclyl) or $R^1$ and $R^2$ or $R^3$ and $R^4$ can combine with the atom(s) to which they are attached to form a 3- to 6-membered spiro cycloalkyl ring or $R^3$ and $R^5$ or $R^4$ and $R^5$ can combine with the atom(s) to which they are attached to form a 4- to 6-membered heterocyclyl ring,
$R^5$ is H, amino, $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_1$-$C_6$ alkylene(aryl), $C_1$-$C_6$ alkylene(heterocyclyl), aryl, or heterocyclyl,
$R^6$ is wherein n is 0, 1, or 2,
X is N or $CR^7$,
$R^7$ is H, halo, or $C_1$-$C_6$ alkyl, and
Ring A is a 5- or 6-membered aryl or heterocyclyl ring, optionally substituted by 1-3 $R^8$ moieties,
$R^8$ is H, halo, nitro, —$CHR^9S(O)_2R^{10}$, —$NR^{10}R^{11}$, —$NR^9S(O)_2R^{10}$, or $NR^9S(O)_2NR^{10}R^{11}$, wherein $R^9$, $R^{10}$, and $R^{11}$ are independently H, $C_1$-$C_6$ alkyl, $C_3$-$C_8$ cycloalkyl, aryl, or heterocyclyl, or $R^9$ and $R^{10}$ or $R^{10}$ and $R^{11}$ combine with the atom(s) to which they are attached to form a 5- or 6-membered heterocyclyl ring,
wherein the above alkyl, alkenyl, alkynyl, aryl, cycloalkyl, or heterocyclyl moieties provided in $R^1$, $R^2$, $R^3$, $R^4$, $R^5$, $R^7$, $R^9$, $R^{10}$, and $R^{11}$ are each optionally and independently substituted by 1-3 substituents selected from
alkoxy,
alkylamine,
amino,
aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
  carboxyl,
  cyano,
  halo,
  hydroxy,
  nitro,
  oxo,
  —C(O)OH, —C(O)$_2$($C_1$-$C_6$ alkyl), —C(O)$_2$($C_3$-$C_8$ cycloalkyl), —C(O)$_2$(aryl), —C(O)$_2$(heterocyclyl), —C(O)$_2$($C_1$-$C_6$ alkylene)aryl, —C(O)$_2$($C_1$-$C_6$ alkylene)heterocyclyl, —C(O)$_2$($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene) heterocyclyl, and —C(O)($C_1$-$C_6$ alkylene)cycloalkyl, wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt, hydrate, tautomer or stereoisomer thereof In one embodiment, the invention relates to compounds of Formula I wherein $R^1$, $R^2$, $R^3$, and $R^4$ are independently H, halo, cyano, $C_1$-$C_6$ hydroxyalkyl, $C_1$-$C_6$ alkoxy, $C_1$-$C_6$ alkyl, $C_3$-$C_8$ cycloalkyl, $C_1$-$C_6$ alkylene(cycloalkyl), $C_2$-$C_6$ alkenyl, $C_2$-$C_6$ alkynyl, aryl, $C_1$-$C_6$ alkylene(aryl), heterocyclyl, or $C_1$-$C_6$ alkylene(heterocyclyl) or $R^1$ and $R^2$ or $R^3$ and $R^4$ can combine with the atom(s) to which they are attached to form a 3- to 6-membered spiro cycloalkyl ring or $R^3$ and $R^5$ or $R^4$ and $R^5$ can combine with the atom(s) to which they are attached to form a 4- to 6-membered heterocyclyl ring.

In another embodiment, the invention relates to compounds of Formula I wherein $R^1$, $R^2$, $R^3$, and $R^4$ are independently selected from

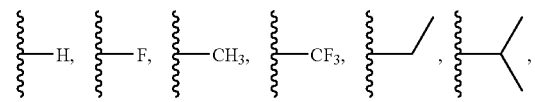

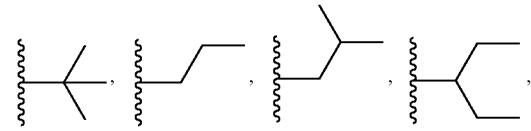

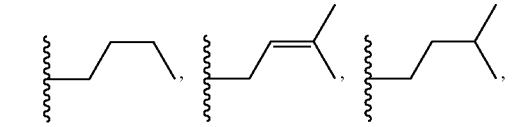

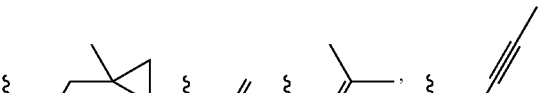

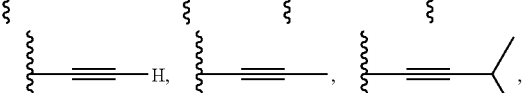

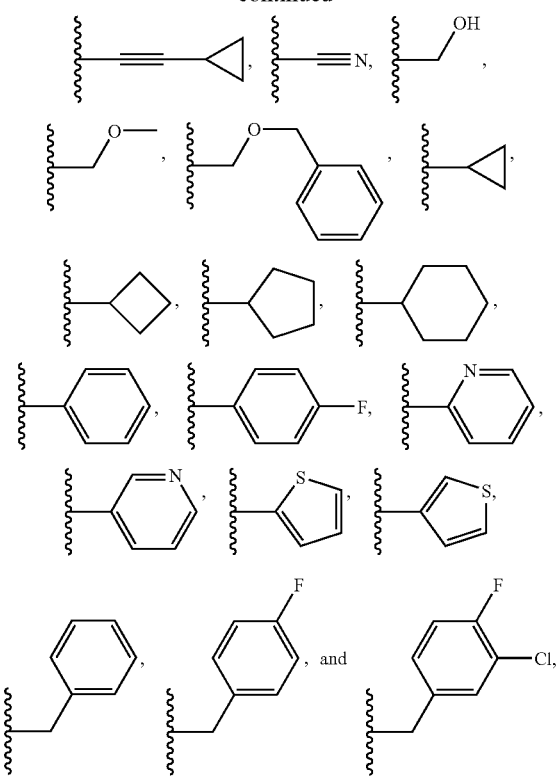

or $R^1$ and $R^2$ or $R^3$ and $R^4$ can combine with the atom(s) to which they are attached to form Spiro rings from

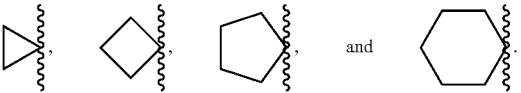

In a further embodiment, the invention relates to compounds of Formula I wherein $R^1$, $R^2$, $R^3$, and $R^4$ are independently selected from

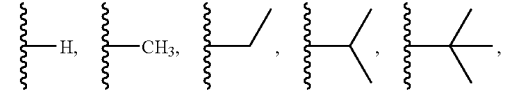

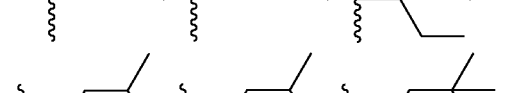

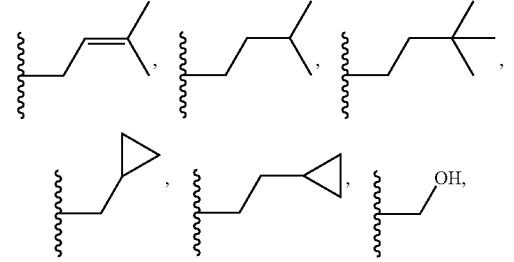

-continued

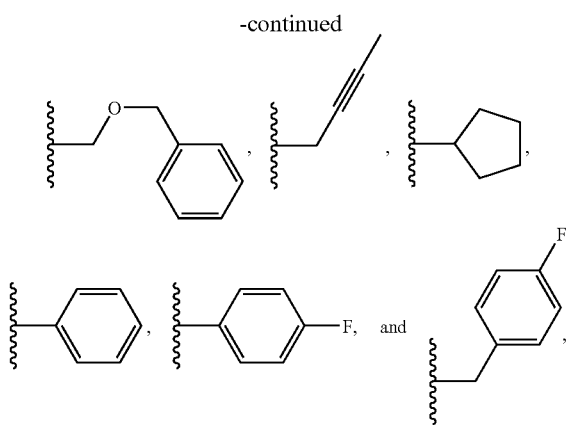

or $R^1$ and $R^2$ or $R^3$ and $R^4$ can combine with the atom(s) to which they are attached to form Spiro rings selected from

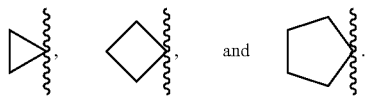

In one embodiment, the invention relates to compounds of Formula I wherein $R^5$ is $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_1$-$C_6$ alkylene(aryl), aryl, or heterocyclyl.

In another embodiment, the invention relates to compounds of Formula I wherein $R^5$ is selected from

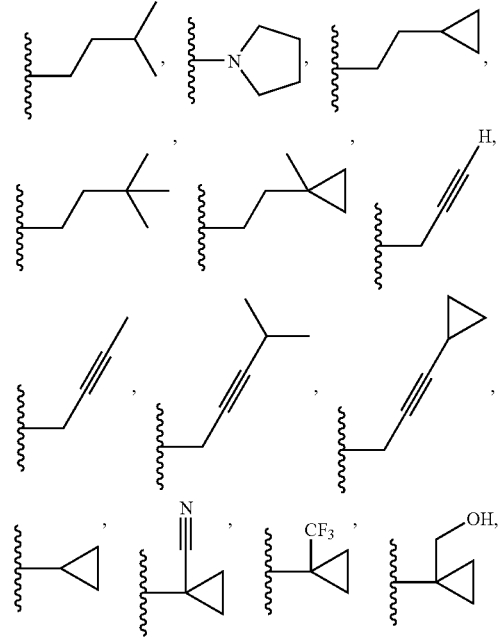

-continued

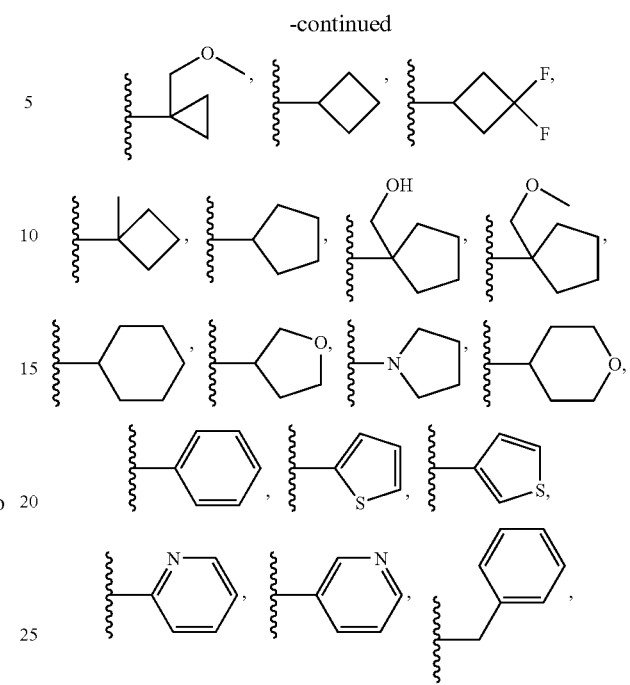

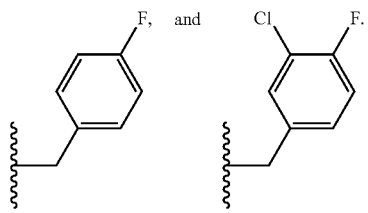

In a further embodiment, the invention relates to compounds of Formula I wherein $R^5$ is selected from

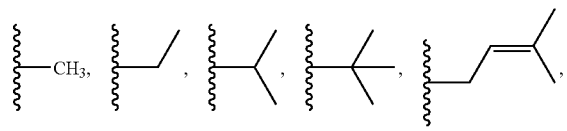

In yet another embodiment, the invention relates to compounds of Formula I wherein $R^3$ and $R^5$ or $R^4$ and $R^5$ combine to form a 4- to 6-membered heterocyclyl ring.

In one embodiment, the invention relates to compounds of Formula I wherein $R^6$ is selected from

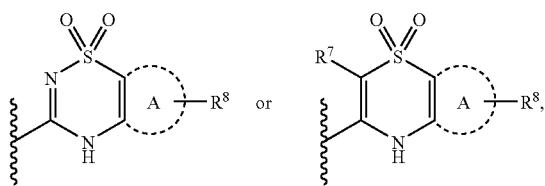

wherein $R^7$ is H.

In a further embodiment, the invention relates to compounds of Formula I wherein $R^6$ is

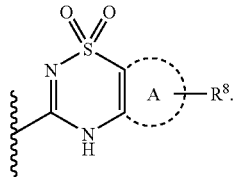

In one embodiment, the invention relates to compounds of Formula I wherein Ring A is selected from

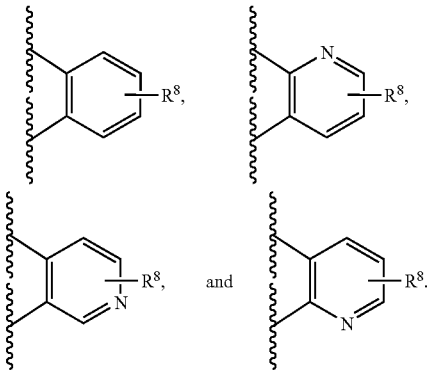

In another embodiment, the invention relates to compounds of Formula I wherein Ring A is selected from

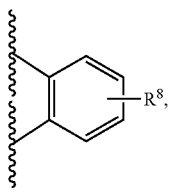

wherein $R^8$ is —$CHR^9S(O)_2R^{10}$, —$NR^{10}R^{11}$, —$NR^9S(O)_2R^{10}$, or $NR^9S(O)_2NR^{10}R^{11}$, wherein $R^9$, $R^{10}$, and $R^{11}$ are independently H, $C_1$-$C_6$ alkyl, $C_3$-$C_8$ cycloalkyl, aryl, or heterocyclyl, or $R^9$ and $R^{10}$ or $R^{10}$ and $R^{11}$ combine with the atom(s) to which they are attached to form a 5- or 6-membered heterocyclyl ring.

In a further embodiment, the invention relates to compounds of Formula I wherein $R^8$ is selected from

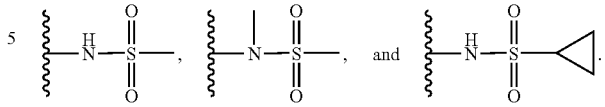

In yet another embodiment, the invention relates to compounds of Formula I wherein $R^8$ is

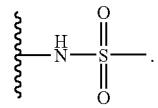

In one embodiment, the invention relates to compounds of Formula I selected from N-{3-[1-(4-Fluoro-benzyl)-4-hydroxy-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-5-methyl-1,5-bis-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[5-(4-Fluoro-benzyl)-8-hydroxy-6-oxo-5-aza-spiro[2.5]oct-7-en-7-yl]-1,1-dioxo-1,4-dihydro-1$\lambda^6$-benzo[1,2,4]thiadiazin-7-yl}-methanesulfonamide, N-{3-[6-(4-Fluoro-benzyl)-9-hydroxy-7-oxo-6-aza-spiro[4.5]dec-8-en-8-yl]-1,1-dioxo-1,4-dihydro-1$\lambda^6$-benzo[1,2,4]thiadiazin-7-yl}-methanesulfonamide, N-{3-[5-Hydroxy-8-methyl-8-(3-methyl-butyl)-7-oxo-1,2,3,7,8,8a-hexahydro-indolizin-6-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-6-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-5-methyl-5-(3-methyl-butyl)-2-oxo-1-pyrrolidin-1-yl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-5-(3-methyl-but-2-enyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-5,5-dimethyl-1-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[7-(4-Fluoro-benzyl)-10-hydroxy-8-oxo-7-aza-spiro[4.5]dec-9-en-9-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-5,5-dimethyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1,5-Bis-(4-fluoro-benzyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-5-methyl-2-oxo-5-phenyl-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopentyl-5-(4-fluoro-benzyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-[3-(1-Cyclopentyl-4-hydroxy-5,5-dimethyl-2-oxo-1,2,5,6-tetrahydro-pyridin-3-yl)-1,1-dioxo-1,4-dihydro-1λ⁶-benzo[1,2,4]thiadiazin-7-yl]-methanesulfonamide, N-{3-[1-Cyclohexyl-5-(4-fluoro-benzyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopropyl-5-(4-fluoro-benzyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopentyl-4-hydroxy-5-(3-methyl-but-2-enyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopentyl-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[6-(4-Fluoro-benzyl)-9-hydroxy-7-oxo-6-aza-spiro[3.5]non-8-en-8-yl]-1,1-dioxo-1,4-dihydro-1λ⁶-benzo[1,2,4]thiadiazin-7-yl}-methanesulfonamide, N-{3-[5-Cyclopropylmethyl-1-(4-fluoro-benzyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-[3-(5-But-2-ynyl-1-cyclopentyl-4-hydroxy-5-methyl-2-oxo-1,2,5,6-tetrahydro-pyridin-3-yl)-1,1-dioxo-1,4-dihydro-1λ⁶-benzo[1,2,4]thiadiazin-7-yl]-methanesulfonamide, N-{3-[1-Cyclohexyl-4-hydroxy-5-methyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclobutyl-4-hydroxy-5-methyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[4-Hydroxy-5-methyl-5-(3-methyl-butyl)-2-oxo-1-phenyl-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[5-Cyclopentyl-1-(3,3-dimethyl-butyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclobutyl-5-(3,3-dimethyl-butyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-[3-(1-Cyclobutyl-4-hydroxy-5-methyl-2-oxo-5-phenyl-1,2,5,6-tetrahydro-pyridin-3-yl)-1,1-dioxo-1,4-dihydro-1λ⁶-benzo[1,2,4]thiadiazin-7-yl]-methanesulfonamide, N-{3-[6-(1-Ethyl-propyl)-1-(4-fluoro-benzyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[6-Ethyl-1-(4-fluoro-benzyl)-4-hydroxy-2-oxo-1,2,5,6-tetrahydro-pyridin-3-yl]-1,1-dioxo-1,4-dihydro-1λ⁶-benzo [1,2,4]thiadiazin-7-yl}-methanesulfonamide, N-{3-[1-Cyclopentyl-5-ethyl-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-6(R)-isopropyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[8-(4-Fluoro-benzyl)-5-hydroxy-8-methyl-7-oxo-1,2,3,7,8,8a-hexahydro-indolizin-6-yl]-1,1-dioxo-1,4-dihydro-1λ⁶-benzo[1,2,4]thiadiazin-7-yl}-methanesulfonamide, N-{3-[1-Cyclobutyl-5-(2-cyclopropyl-ethyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopentyl-5-(2-cyclopropyl-ethyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-2-oxo-6-phenyl-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[6(R)-Ethyl-1-(4-fluoro-benzyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopentyl-5-(3,3-dimethyl-butyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-3-[1-Cyclohexyl-5-(3,3-dimethyl-butyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-Cyclopropyl-5-(3,3-dimethyl-butyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[6(R)-tert-Butyl-1-(4-fluoro-benzyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-6-(4-fluoro-phenyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[5-Ethyl-1-(4-fluoro-benzyl)-4-hydroxy-5-methyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[6(S)-Ethyl-1-(4-fluoro-benzyl)-4-hydroxy-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[4-Hydroxy-1-(3-methyl-butyl)-2-oxo-6(R)-phenyl-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-2-oxo-6(R)-phenyl-1,2,5,6-tetrahydro-pyridin-3-yl]-1,1-dioxo-1,4-dihydro-1λ⁶-benzo[1,2,4]thiadiazin-7-yl}-methanesulfonamide,
N-[3-(5-Butyl-1-cyclobutyl-4-hydroxy-5-methyl-2-oxo-1,2,5,6-tetrahydro-pyridin-3-yl)-1,1-dioxo-1,4-dihydro-1λ⁶-benzo[1,2,4]thiadiazin-7-yl]-methanesulfonamide,
N-[3-(1-Cyclobutyl-4-hydroxy-5-methyl-2-oxo-5-propyl-1,2,5,6-tetrahydro-pyridin-3-yl)-1,1-dioxo-1,4-dihydro-1λ⁶-benzo[1,2,4]thiadiazin-7-yl]-methanesulfonamide,
N-{3-[1-Cyclopentyl-4-hydroxy-6-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide,
N-{3-[1-Cyclopentyl-4-hydroxy-5-hydroxymethyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide,
N-{3-[1-(3-Chloro-4-fluoro-benzyl)-4-hydroxy-6(R)-isopropyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide,
N-[3-(1-Cyclopentyl-4-hydroxy-6-isobutyl-2-oxo-1,2,5,6-tetrahydro-pyridin-3-yl)-1,1-dioxo-1,4-dihydro-1λ⁶-benzo[1,2,4]thiadiazin-7-yl]-methanesulfonamide, and
N-{3-[1-(4-Fluoro-benzyl)-4-hydroxy-6-isobutyl-2-oxo-1,2,5,6-tetrahydro-pyridin-3-yl]-1,1-dioxo-1,4-dihydro-1λ⁶-benzo[1,2,4]thiadiazin-7-yl}-methanesulfonamide
N-{3-[5-Benzyloxymethyl-1-cyclopentyl-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide.

The invention is also directed to pharmaceutically acceptable salts, and pharmaceutically acceptable solvates of the compounds of Formula I. Advantageous methods of making the compounds of Formula I are also described.

In one aspect, the invention encompasses a method for treating or preventing hepatitis C virus infection in a mammal in need thereof, preferably in a human in need thereof, comprising administering to the patient a therapeutically or prophylactically effective amount of a Formula I compound. In one embodiment, the invention encompasses a method for treating or preventing hepatitis C virus infection by administering to a patient in need thereof a therapeutically or prophylactically effective amount of a Formula I compound that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent or an immunomodulatory agent.

DETAILED DESCRIPTION OF THE INVENTION

Where the following terms are used in this specification, they are used as defined below:

The terms "comprising," "having" and "including" are used herein in their open, non-limiting sense.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkylene", as used herein, unless otherwise indicated, includes a divalent radical derived from alkyl, as exemplified by —CH₂CH₂CH₂CH₂—.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3-10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

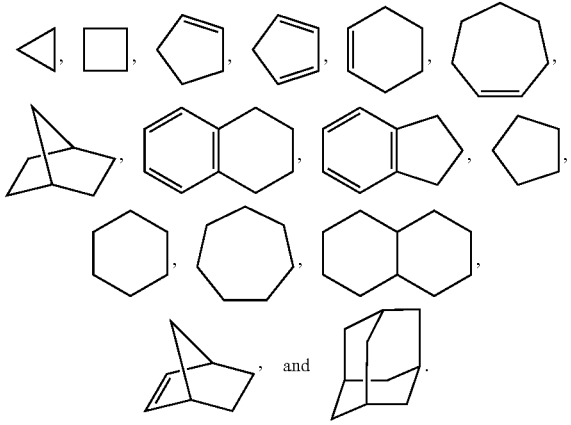

The term "aryl", as used herein, unless otherwise indicated, includes an organic radical derived from an aromatic hydrocarbon by removal of one hydrogen, such as phenyl or naphthyl.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

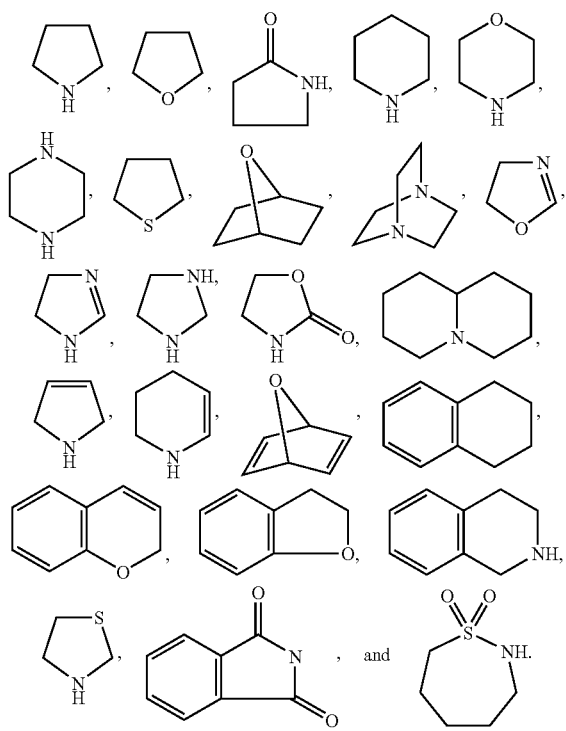

Unless defined otherwise, "alkyl," "alkylene," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$($C_1$-$C_6$ alkyl), —C(O)$_2$($C_3$-$C_8$ cycloalkyl), —C(O)$_2$(aryl), —C(O)$_2$(heterocyclyl), —C(O)$_2$($C_1$-$C_6$ alkylene)aryl, —C(O)$_2$($C_1$-$C_6$ alkylene)heterocyclyl, —C(O)$_2$($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

preventing a disease, disorder, or condition from occurring in an animal that may be predisposed to the disease, disorder and/or condition, but has not yet been diagnosed as having it;

inhibiting the disease, disorder, or condition, i.e., arresting its development; and relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac-(or racem-) or by the symbols RS and SR.

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

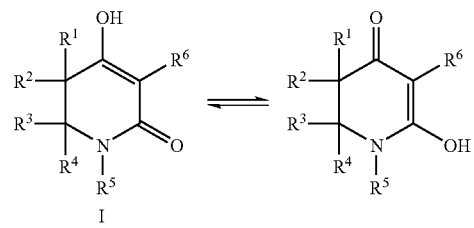

For $R^6$, wherein $X = N$ and $n = 2$:

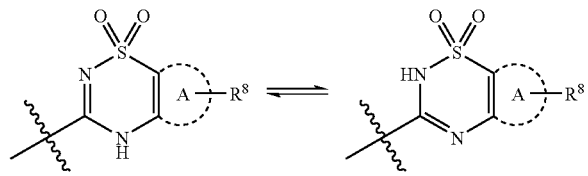

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal, co-crystal, or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll-like receptor modulators. In one embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an anti-emetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compound s of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the α-interferons; β-interferons; adefovir, clevadine, entecavir, pleconaril.

The Formula I compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll-like receptor (TLR) modulators. Examples of cytokine receptor modulators include, but are not limited to, soluble cytokine receptors (e.g., the extracellular domain of a TNF-a receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-a antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061, SCH-503034, ITMN-191 or VX-950; and inhibitors of NS5b polymerase such as NM107 (and its prodrug NM283), R1626, R7078, BILN1941, GSK625433, GILD9128 or HCV-796.

The Formula I compounds of the invention can be administered or formulated in combination with an agent which inhibits HCV polymerase such as those described in Wu, *Curr Drug Targets Infect Disord.* 2003; 3(3):207-19 or in combination with compounds that inhibit the helicase function of the virus such as those described in Bretner M, et al *Nucleosides Nucleotides Nucleic Acids.* 2003; 22(5-8):1531, or with inhibitors of other HCV specific targets such as those described in Zhang X., *IDrugs,* 5(2), 154-8 (2002).

The Formula I compounds of the invention can be administered or formulated in combination with an agent which inhibits viral replication.

The Formula I compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-1 8), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I compounds of the invention can be administered or formulated in combination with β-interferons which include, but are not limited to, interferon β-1a, interferon β-1b.

The Formula I compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.,* 7-1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingelheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a Formula I compound to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula I compounds to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference) A Formula I compound can also be formulated in rectal or vaginal compositions such as suppositories or retention enemas, e.g., containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.*, 1987, 14, 201; Buchwald et al., *Surgery*, 1980, 88, 507; Saudek et al., *N. Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25,351; Howard et al., *J. Neurosurg.*, 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous sodium sulfate and/or magnesium sulfate prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO flash column chromatography using prepacked RediSep silica gel columns, or Analogix flash column chromatography using prepacked SuperFlash silica gel columns. Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers (cm$^{-1}$). Mass spectra reported are (+)-ESI or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures may utilize many common chemical abbreviations, 2,2-DMP (2,2-dimethoxypropane), Ac (acetyl), ACN (acetonitrile), Bn (benzyl), BnOH (benzyl alcohol), Boc (tert-butoxycarbonyl), Boc$_2$O (di-tert-butyl dicarbonate), Bz (benzoyl), CSI (chlorosulfonyl isocyanate), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIBAL (diisobutylaluminum hydride), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC or EDCI (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), KN(TMS)$_2$ (potassium bis(trimethylsilyl)amide), KO$^t$Bu (potassium tert-butoxide), LDA (lithium diisopropylamine), LiHMDS (lithium bis(trimethylsilyl)amide), MCPBA (3-chloroperbenzoic acid), Me (methyl), MeCN (acetonitrile), MeOH (methanol), NaBH$_3$CN (sodium cyanoborohydride), NaH (sodium hydride), NaN(TMS)$_2$ (sodium bis(trimethylsilyl)amide), NaOAc (sodium acetate), Na(OAc)$_3$BH (sodium triacetoxyborohydride), NaOEt (sodium ethoxide), NMM (N-methylmorpholine), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydro furan), TLC (thin layer chromatography), Tol (toluoyl), Val (valine), Xantphos (4,5-bis(diphenylphosphino)-9,9-dimethylxanthene), and the like.

Scheme 1 provides a general procedure that can be used to prepare compounds and intermediates of the invention as described by Formula I. β-Amino esters (or their salts, such as hydrochlorides) can undergo reactions with aldehydes or ketones, where $R^X$ and $R^W$ are $C_1$-$C_5$ alkyl, $C_3$-$C_8$ cycloalkyl, $C_1$-$C_5$ alkylene($C_3$-$C_8$ cycloalkyl), $C_1$-$C_5$ alkylene(aryl), $C_1$-$C_5$ alkylene(heterocyclyl), aryl, or heterocyclyl, or $R^W$ can combine with $R^X$ to form a 3- to 6-membered ring to give intermediate imines or enamines that can undergo subsequent hydrogenation with reducing agents, such as sodium cyanoborohydride, to provide N-monoalkylated β-amino esters. Treatment of β-amino esters of this type with a strong base, such as potassium bis(trimethylsilyl)amide, followed by treatment with an appropriate alkylating agent, such as an alkyl halide, gives C-monoalkylated β-amino esters. Further elucidation of the β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium hydride, gives the desired target molecules.

Scheme 1

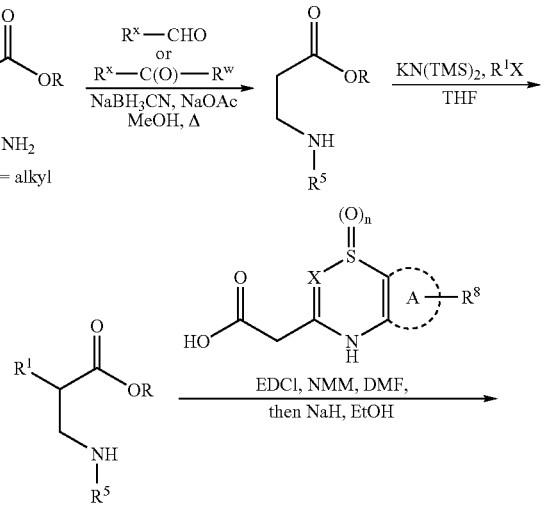

-continued

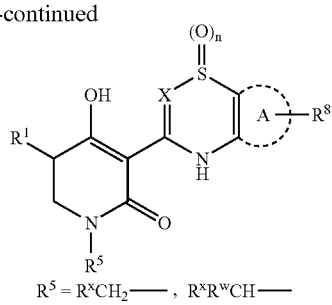

$R^5 = R^xCH_2$——, $R^xR^wCH$——

Example 1

N-{3-[1-(4-Fluoro-benzyl)-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide

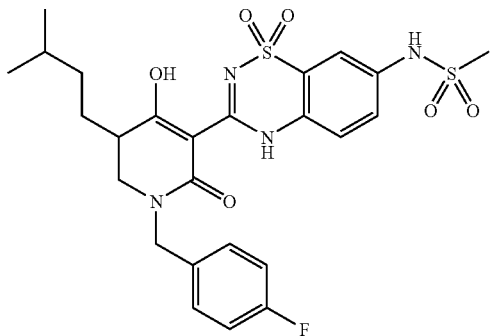

3-(4-Fluoro-benzylamino)-propionic Acid Ethyl Ester

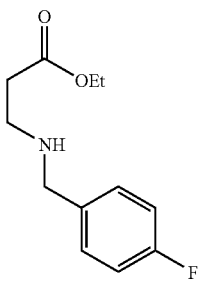

A suspension of β-alanine ethyl ester hydrochloride salt (2.0 g, 13.0 mmol), 4-fluorobenzaldehyde (1.61 g, 13.0 mmol), sodium acetate (2.13 g, 26.0 mmol), and 4 Å molecular sieves (0.5 g/mmol) in methanol (50 mL) was treated with sodium cyanoborohydride (1.63 g, 26.0 mmol). The reaction was stirred at 25° C. for 4 h, diluted with a saturated aqueous sodium bicarbonate solution (150 mL), and extracted with ethyl acetate (3×50 mL). The combined organic layers were dried over magnesium sulfate, filtered, and concentrated in vacuo. The crude oil was purified by flash column chromatography (ISCO RediSep column, 20 to 70% ethyl acetate in hexanes) to give 3-(4-fluoro-benzylamino)-propionic acid ethyl ester (2.08 g, 71%) as a colorless oil. $^1$H NMR (400 MHz, CDCl$_3$) δ: 1.26 (t, 3H, J=7.0 Hz), 2.52 (t, 2H, J=6.5 Hz), 2.88 (t, 2H, J=6.2 Hz), 3.76 (s, 2H), 4.14 (q, 2H, J=6.8 Hz), 6.96-7.01 (m, 2H), 7.26-7.28 (m, 2H). LC-MS (ESI) calculated for $C_{12}H_{11}FNO_2$: 225.3, found 226.2 [M+H$^+$].

b) 2-[(4-Fluoro-benzylamino)-methyl]-5-methyl-hex-4-enoic Acid Ethyl Ester

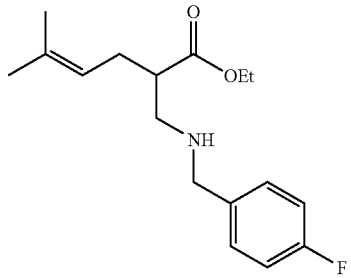

A solution of 3-(4-fluoro-benzylamino)-propionic acid ethyl ester (158 mg, 0.701 mmol) in anhydrous tetrahydrofuran (8 mL) was stirred under an environment of nitrogen at −78° C. and treated via syringe with 0.5 M in toluene potassium bis(trimethylsilyl)-amide (1.4 mL, 0.701 mmol). After 15 min, 4-bromo-2-methyl-2-butene (104 mg, 0.701 mmol) was added and the reaction mixture was stirred at −78° C. for 6 h. The reaction was allowed to warm to 25° C. and was diluted with a saturated aqueous sodium bicarbonate solution (25 mL) and extracted with ethyl acetate (3×50 mL). The combined organic layers were dried over magnesium sulfate, filtered, and concentrated in vacuo. The crude oil was purified by flash column chromatography (ISCO RediSep column, 5 to 60% ethyl acetate in hexanes) to give 2-[(4-fluoro-benzylamino)-methyl]-5-methyl-hex-4-enoic acid ethyl ester (181 mg, 37%) as a colorless oil. $^1$H NMR (400 MHz, CDCl$_3$) δ: 1.25 (t, 3H, J=7.0 Hz), 1.60 (s, 3H), 1.68 (s, 3H), 2.18-2.25 (m, 1H), 2.28-2.37 (m, 1H), 2.55-2.62 (m, 1H), 2.69 (dd, 1H, J$_1$=11.7 Hz, J$_2$=4.7 Hz), 2.86 (dd, 1H, J$_1$=11.7 Hz, J$_2$=8.6 Hz), 3.67-3.81 (m, 2H), 4.10-4.18 (m, 2H), 5.04-5.08 (m, 1H), 6.98 (t, 2H, J=8.5 Hz), 7.23-7.27 (m, 2H). LC-MS (ESI) calculated for $C_{17}H_{24}FNO_2$: 293.4, found 294.5 [M+H$^+$].

c) 2-Chloro-5-nitrobenzenesulfonamide

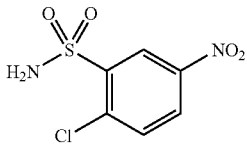

To a solution of thionyl chloride (11 mL) and 2-chloro-5-nitro-benzenesulfonic acid (4.78 g, 20.1 mmol) was added N,N-dimethylformamide (0.92 µL) and the reaction mixture was heated to reflux for 4 h. Upon cooling, the reaction mixture was azeotroped with toluene (2-3×). The sulfonyl chloride was dissolved in a minimal amount of toluene and then added to a mixture of concentrated aqueous ammonium hydroxide solution (25 mL) and tetrahydrofuran (25 mL) at −10° C. After stirring for 2 h the reaction was quenched by adding a 6.0 M aqueous hydrochloric acid solution until pH 4 was reached. The layers were separated and the organic layer was concentrated in vacuo to a slurry. Pentane was added and the product was isolated by vacuum filtration to afford the desired product, 2-chloro-5-nitrobenzenesulfonamide (2.0 g, 8.48 mmol, 42.4% yield) as a solid.

d) 2-Amino-5-nitrobenzenesulfonamide

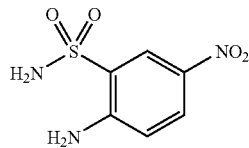

A mixture of 2-chloro-5-nitrobenzenesulfonamide (0.88 g, 3.72 mmol), ammonium carbonate (0.88 g, 9.16 mmol), and copper(II)sulfate (0.175 g, 1.10 mmol) in concentrated aqueous ammonium hydroxide solution (4.4 mL) was heated for 4 h at 120° C. in a pressure reaction vessel. The mixture was allowed to cool to 25° C. and the resulting solid was collected by vacuum filtration, washed with water and dried to afford the desired product, 2-amino-5-nitrobenzenesulfonamide (0.295 g, 1.36 mmol, 36.5% yield) as a tan solid.

e) 2,5-Diaminobenzenesulfonamide

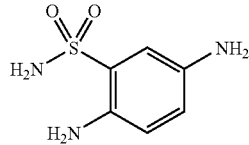

A mixture of 2-amino-5-nitrobezenesulfonamide (10 g, 46.08 mmol), 10% palladium on charcoal (~1 g) in tetrahydrofuran (250 mL) was hydrogenated for 26 h at 25° C. under 1 atmosphere of hydrogen gas via balloon. The mixture was then filtered through Celite, washed with tetrahydrofuran, and the solvent removed in vacuo to afford the desired product. The catalyst/Celite mixture was slurried in methanol (400 mL) for 16 h, filtered and the solvent was removed in vacuo to afford a second batch of the desired product, 2,5-diaminobenzenesulfonamide (combined: 7.79 g, 41.65 mmol, 90.4% yield) as a light-brown solid. $^1$H NMR (400 MHz, DMSO-$d_6$) δ: 4.54 (2H, bs), 4.98 (2H, bs), 6.55-6.60 (2H, m), 6.87 (1H, d, J=2.2 Hz), 6.99 (2H, bs). LC-MS (ESI) calcd for $C_6H_9N_3O_2S$ 187.04, found 188.3 [M+H$^+$].

f) 2-Amino-5-methanesulfonylamino-benzenesulfonamide

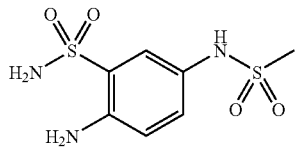

2,5-Diaminobenzenesulfonamide (11.16 g, 59.61 mmol) was dissolved in acetonitrile (300 mL) and pyridine (7.07 g, 89.41 mmol) was added. Methanesulfonyl chloride (7.17 g, 62.59 mmol) was added dropwise over a period of 10 min and the reaction mixture was stirred for 16 h at 25° C. after which time a precipitate had formed. Most of the acetonitrile was removed in vacuo and water (200 mL) was added to afford a clear solution. The product slowly started to precipitate and the mixture was placed in an ice bath for 3 h. The precipitate was collected by vacuum filtration and dried under high vacuum to afford the desired product, 2-amino-5-methanesulfonylamino-benzenesulfonamide (11.1 g, 41.84 mmol, 70.2% yield) as a brown solid. $^1$H NMR (400 MHz, CD$_3$OD) δ: 2.89 (3H, s), 6.82 (1H, d, J=8.5 Hz), 7.20 (1H, dd, $J_1$=8.5 Hz, $J_2$=2.5 Hz), 7.58 (1H, d, J=2.5 Hz). LC-MS (ESI) calcd for $C_7H_{11}N_3O_4S_2$ 265.02, found 266.0 [M+H$^+$].

g) N-(4-Methanesulfonylamino-2-sulfamoyl-phenyl)-malonamic Acid Ethyl Ester

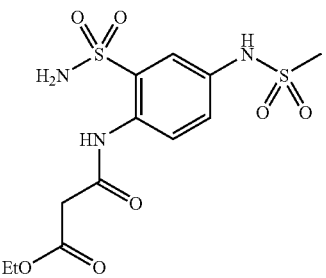

2-Amino-5-methanesulfonylamino-benzenesulfonamide (23.27 g, 87.81 mmol) was dissolved in N,N-dimethylacetamide (100 mL) and diethyl ether (100 mL). Ethyl 3-chloro-3-oxo-propionate (13.88 g, 92.20 mmol) was added and the reaction mixture was stirred at 25° C. for 1 h. The reaction mixture was diluted with ethyl acetate (400 mL) and was extracted with water (400 mL). The aqueous layer was back-extracted with ethyl acetate (2×200 mL). The combined organic layers were dried over sodium sulfate, filtered and most of the solvent was removed in vacuo to a volume of ~100 mL. To the stirred solution was added hexanes (~100 mL) upon which a precipitate formed. The precipitate was collected by vacuum filtration, washed with hexanes and dried under high vacuum to afford the analytically pure product, N-(4-methanesulfonylamino-2-sulfamoyl-phenyl)-malonamic acid ethyl ester (31.22 g, 85.53 mmol, 97.4% yield) as a light-brown solid. $^1$H NMR (400 MHz, CD$_3$OD) δ: 1.31 (3H, t, J=7.0 Hz), 3.00 (3H, s), 3.59 (2H, s), 4.25 (2H, quartet, J=6.9 Hz), 7.42-7.45 (1H, m), 7.86 (1H, m), 7.92 (1H, d, J=8.8 Hz).

h) (7-Methanesulfonylamino-1,1-dioxo-1,4-dihydro-1λ$^6$-benzo[1,2,4]thiadiazin-3-yl)-acetic Acid

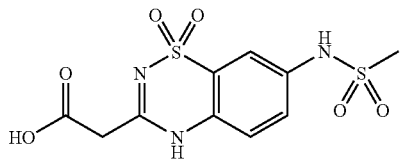

N-(4-Methanesulfonylamino-2-sulfamoyl-phenyl)-malonamic acid ethyl ester (9.55 g, 26.16 mmol) was dissolved in 8% aqueous sodium hydroxide solution (262 mL) and heated at 100° C. for 1.5 h. The reaction mixture was cooled to 0° C. and the solution was acidified by slowly adding 12.0 M aqueous hydrochloric acid solution until pH 1-2 was reached. A precipitate started to form and the suspension was allowed to stir for 30 min at 0° C. The precipitate was collected by vacuum filtration, washed with cold water, and dried under high vacuum to afford (7-methanesulfonylamino-1,1-dioxo-1,4-dihydro-1λ⁶-benzo[1,2,4]thiadiazin-3-yl)-acetic acid (7.20 g, 21.621 mmol, 82.6% yield) as a pinkish solid. ¹H NMR (400 MHz, DMSO-$d_6$) δ: 3.03 (3H, s), 3.56 (2H, s), 7.33 (1H, d, J=9.1 Hz), 7.52-7.54 (2H, m), 10.09 (1H, s), 12.24 (1H, s), 13.02 (1H, bs). LC-MS (ESI) calcd for $C_{10}H_{11}N_3O_6S_2$ 333.01, found 334.1 [M+H⁺].

N-{3-[1-(4-Fluoro-benzyl)-4-hydroxy-5-(3-methyl-but-2-enyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide

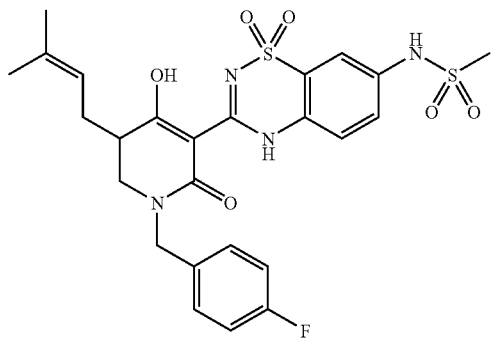

A solution of 2-[(4-fluoro-benzylamino)-methyl]-5-methyl-hex-4-enoic acid ethyl ester (102 mg, 0.35 mmol), (7-methanesulfonylamino-1,1-dioxo-1,4-dihydro-1λ⁶-benzo[1,2,4]thiadiazin-3-yl)-acetic acid (115 mg, 0.345 mmol), and 1-(3-dimethylaminopropyl)-3-ethylcarbodiimide hydrochloride (69 mg, 0.36 mmol) in anhydrous N,N-dimethylformamide (5 mL) was treated with N-methylmorpholine. The reaction was stirred for 1 h at 25° C., diluted with a 1.0 M aqueous hydrochloric acid solution (20 mL), and extracted with ethyl acetate (3×50 mL). The combined organic layers were dried over magnesium sulfate, filtered, and concentrated in vacuo. The residue was dissolved in ethanol (6 mL) and treated with a 60% oil dispersion of sodium hydride (41 mg, 1.74 mmol). The reaction was heated at 70° C. for 1 h, allowed to cool to 25° C., and quenched with a 1.0 M aqueous hydrochloric acid solution (50 mL). The resulting mixture was extracted with ethyl acetate (3×50 mL), and the combined organic layers were dried over magnesium sulfate, filtered, and concentrated in vacuo. The crude oil was purified by flash column chromatography (ISCO RediSep column, 10 to 80% ethyl acetate in hexanes) to give N-{3-[1-(4-fluoro-benzyl)-4-hydroxy-5-(3-methyl-but-2-enyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide (90 mg, 46%) as a light yellow solid. ¹H NMR (400 MHz, CDCl₃) δ: 1.54 (s, 3H), 1.69 (s, 3H), 2.15-2.23 (m, 1H), 2.39-2.44 (m, 1H), 2.60-2.66 (m, 1H), 3.06 (s, 3H), 3.19 (dd, 1H, $J_1$=13.1 Hz, $J_2$=4.3 Hz), 3.45 (dd, 1H, $J_1$=12.4 Hz, $J_2$=5.4 Hz), 4.61 (s, 2H), 4.89 (t, 3H, J=6.6 Hz), 7.05 (t, 2H, J=8.5 Hz), 7.23-7.28 (m, 3H), 7.63-7.66 (m, 1H), 7.69 (d, 1H, J=2.2 Hz). LC-MS (ESI) calculated for $C_{25}H_{27}FN_4O_6S_2$: 562.6, found 563.4 [M+H⁺].

j) N-{3-[1-(4-Fluoro-benzyl)-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide

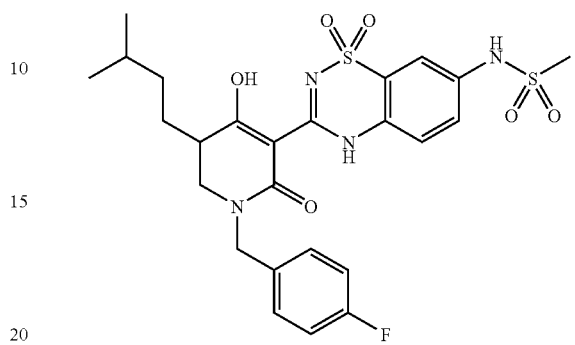

A solution of N-{3-[1-(4-fluoro-benzyl)-4-hydroxy-5-(3-methyl-but-2-enyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide (60 mg, 0.107 mmol) in ethyl acetate (2 mL) was treated with 5 wt % Pd/C (10 mg). The reaction was stirred under a hydrogen environment (1 atm) for 12 h and filtered through Celite. The filtrate was concentrated in vacuo to give N-{3-[1-(4-fluoro-benzyl)-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide (54 mg, 90%) as a white solid. ¹H NMR (400 MHz, CDCl₃) δ: 0.78-0.83 (m, 6H), 0.95-1.12 (m, 2H), 1.31-1.45 (m, 2H), 1.64-1.73 (m, 1H), 2.50-2.55 (m, 1H), 3.06 (s, 3H), 3.18 (dd, 1H, $J_1$=12.7 Hz, $J_2$=4.3 Hz), 3.52 (dd, 1H, $J_1$=12.9 Hz, $J_2$=5.0 Hz), 4.31 (d, 1H, J=14.9 Hz), 4.93 (d, 1H, J=14.7 Hz), 6.84 (br s, 1H), 7.06 (t, 2H, J=8.6 Hz), 7.23-7.29 (m, 3H), 7.64 (dd, 1H, $J_1$=8.7 Hz, $J_2$=2.3 Hz), 7.68 (d, 1H, J=2.3 Hz). LC-MS (ESI) calculated for $C_{25}H_{29}FN_4O_6S_2$: 564.7, found 565.5 [M+H⁺].

Scheme 2 provides a general procedure that can be used to prepare compounds and intermediates of the invention as described by Formula I. Commercially available malonates can be alkylated with a strong base, such as sodium hydride, and a suitable alkylating agent, such as an alkyl halide. Dialkyl malonates can undergo de-symmetrized by treatment with a reducing agent, such as diisobutylaluminum hydride, to provide the corresponding β-formylesters. Also, in some cases 2,2-disubstituted dialkyl malonates are commercially available, and can undergo the reduction described above to furnish the corresponding β-formylesters. Treatment of the resulting β-formylesters with a primary amine gives imines that can undergo subsequent hydrogenation with a reducing agent, such as sodium cyanoborohydride, to provide N-monoalkylated β-amino esters. Further elucidation of the β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium hydride, gives the desired target molecules.

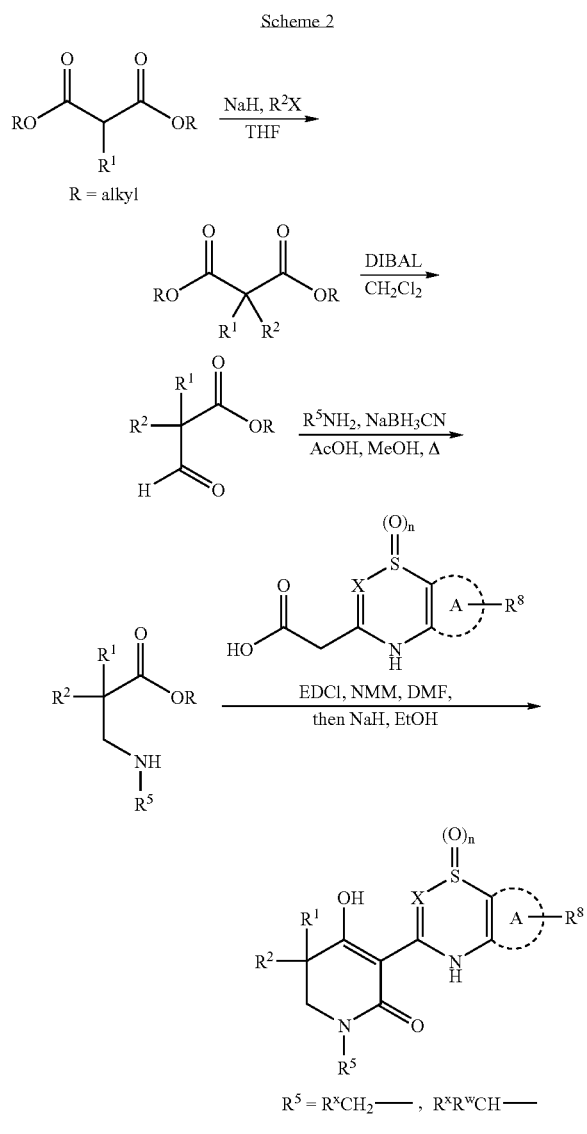

Scheme 2

Example 2

N-{3-[1-(4-Fluoro-benzyl)-4-hydroxy-5-methyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide

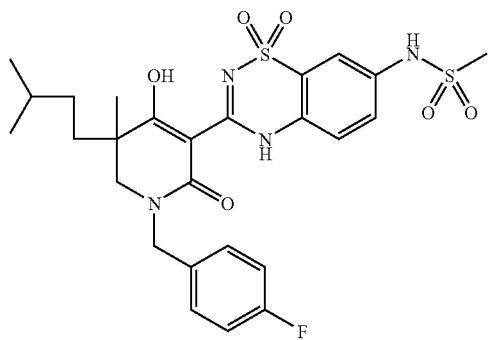

2-Methyl-2-(3-methyl-butyl)-malonic Acid Diethyl Ester

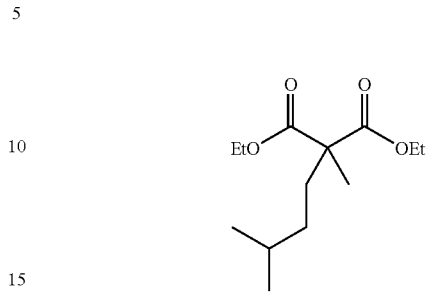

A solution of diethyl isopentylmalonate (2.31 g, 10 mmol) in a 6:2 mixture of anhydrous N,N-dimethylformamide/diethyl ether (8 mL) was stirred under a nitrogen environment at 25° C. and treated with a 60% oil dispersion of sodium hydride (480 mg, 12 mmol). The reaction mixture was stirred until the evolution of hydrogen gas ceased. The reaction was then treated dropwise via syringe with iodomethane (1.87 mL, 30 mmol) and stirred for 3 h at 25° C. The reaction was quenched with a 1.0 M aqueous hydrochloric acid solution (30 mL) and extracted with diethyl ether (2×50 mL). The combined organic layers were washed with a saturated aqueous sodium bicarbonate solution (50 mL) and brine (50 mL), dried over sodium sulfate, filtered, and concentrated in vacuo to give 2-methyl-2-(3-methyl-butyl)-malonic acid diethyl ester (2.09 g, 85%) as a clear oil. $^1$H NMR (400 MHz, CDCl$_3$) δ: 0.88 (d, 6H, J=6.9 Hz), 1.06-1.12 (m, 2H), 1.24 (t, 6H, J=7.0 Hz), 1.38 (s, 3H), 1.51 (septet, 1H, J=6.6 Hz), 1.82-1.87 (m, 2H), 4.12-4.20 (m, 4H). LC-MS (ESI) calculated for C$_{13}$H$_{24}$O$_4$: 244.3, found 245.3 [M+H$^+$].

b) 2-Formyl-2,5-dimethyl-hexanoic Acid Ethyl Ester

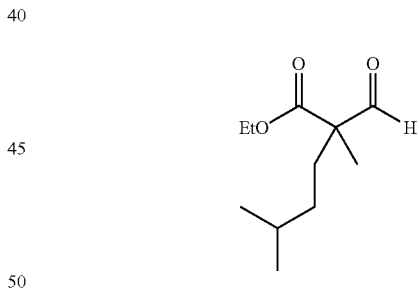

A solution of 2-methyl-2-(3-methyl-butyl)-malonic acid diethyl ester (500 mg, 2.05 mmol) in anhydrous dichloromethane (4 mL) was stirred at −78° C. under a blanket of nitrogen and treated dropwise via syringe with a 1.0 M solution of DIBAL in toluene (4.1 mL, 4.1 mmol) over a period of 15 min. The reaction was stirred for 4 h at −78° C. and quenched sequentially with a saturated aqueous ammonium chloride solution (3 mL) and a 4% aqueous hydrochloric acid solution (3 mL). The resulting gelatinous suspension was allowed to warm to 25° C. and was filtered through a sintered glass funnel. The filtrate was concentrated in vacuo. The resulting crude oil was purified by flash column chromatography (ISCO RediSep column, 0 to 20% ethyl acetate in hexanes) to give 2-formyl-2,5-dimethyl-hexanoic acid ethyl ester (150 mg, 36%) as a clear oil. $^1$H NMR (400 MHz, CDCl$_3$) δ: 0.89 (d, 6H, J=6.9 Hz), 1.07-1.15 (m, 2H), 1.23-

1.26 (m, 3H), 1.28 (s, 3H), 1.52 (septet, 1H, J=6.6 Hz), 1.83-1.92 (m, 2H), 4.21 (q, 2H, J=6.9 Hz), 9.69 (s, 1H).

c) 2-[(4-Fluoro-benzylamino)-methyl]-2,5-dimethyl-hexanoic Acid Ethyl Ester

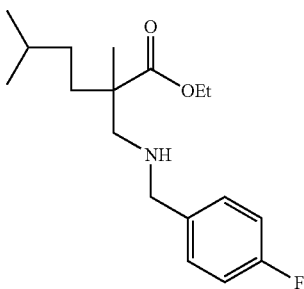

A solution of 2-formyl-2,5-dimethyl-hexanoic acid ethyl ester (126 mg, 0.629 mmol) in ethanol (3 mL) was treated with 4-fluorobenzylamine (87 mg, 0.692 mmol) and stirred at 60° C. for 18 h. The reaction mixture was allowed to cool to 25° C. and treated with glacial acetic acid (0.036 mL, 0.629 mmol) followed by sodium cyanoborohydride (48 mg, 1.26 mmol). The reaction was stirred for 1 h at 25° C., quenched with a 1.0 M aqueous sodium hydroxide solution (2 mL), extracted with ethyl acetate (2×100 mL), washed with brine (100 mL), dried over sodium sulfate, filtered, and concentrated in vacuo. The crude oil was purified by flash column chromatography (ISCO RediSep column, 0 to 40% ethyl acetate in hexanes) to give 2-[(4-fluoro-benzylamino)-methyl]-2,5-dimethyl-hexanoic acid ethyl ester (96 mg, 49%) as a clear oil. $^1$H NMR (400 MHz, CDCl$_3$) δ: 0.87 (d, 6H, J=6.0 Hz), 1.00-1.14 (m, 2H), 1.17 (s, 3H), 1.24 (t, 3H, J=7.0 Hz), 1.40-1.49 (m, 3H), 1.60 (sextet, 1H, J=6.1 Hz), 2.65 (dd, 2H, J$_1$=108.4 Hz, J$_2$=11.7, Hz), 3.74 (s, 2H), 4.12 (q, 2H, J=7.1 Hz), 6.98 (t, 2H, J=8.6 Hz), 7.26 (q, 2H, J=4.7 Hz). LC-MS (ESI) calculated for C$_{18}$H$_{28}$FNO$_2$: 309.4, found 310.3 [M+H$^+$].

d) N-{3-[1-(4-Fluoro-benzyl)-4-hydroxy-5-methyl-5-(3-methyl-butyl)-2-oxo-1,2,5,6-tetrahydro-pyridin-3-yl]-1,1-dioxo-1,4-dihydro-1λ$^6$-benzo[1,2,4]thiadi-azin-7-yl}-methanesulfonamide

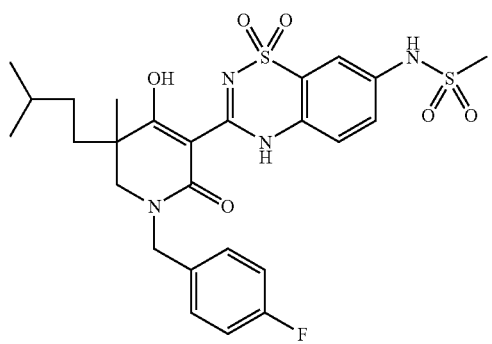

A solution of 2-[(4-fluoro-benzylamino)-methyl]-2,5-dimethyl-hexanoic acid ethyl ester (93 mg, 0.30 mmol), (7-methanesulfonylamino-1,1-dioxo-1,4-dihydro-1λ$^6$-benzo[1,2,4]thiadiazin-3-yl)-acetic acid (100 mg, 0.30 mmol), and 1-(3-dimethylaminopropyl)-3-ethylcarbodiimide hydrochloride (60 mg, 0.315 mmol) in anhydrous N,N-dimethyformamide (4 mL) was treated with N-methyl morpholine (0.069 mL, 0.63 mmol). The reaction was stirred under a nitrogen environment at 25° C. for 1 h, quenched with a 1.0 M aqueous hydrochloric acid solution (50 mL), extracted with ethyl acetate (2×50 mL), dried over sodium sulfate, filtered, and concentrated in vacuo. The resulting oil was dissolved in ethanol (5 mL) and treated with a 60% oil dispersion of sodium hydride (48 mg, 2.0 mmol). The reaction was heated at 60° C. under a nitrogen environment for 1.5 h. The reaction mixture was allowed to cool to 25° C., quenched with a 0.5 M aqueous hydrochloric acid solution (50 mL), extracted with ethyl acetate (2×50 mL), washed with brine (50 mL), dried with sodium sulfate, filtered, and concentrated in vacuo. The crude resin was purified by flash column chromatography (ISCO RediSep column, 0 to 100% ethyl acetate in hexanes) to afford the desired product, N-{3-[1-(4-fluoro-benzyl)-4-hydroxy-5-methyl-5-(3-methyl-butyl)-2-oxo-1,2,5,6-tetrahydro-pyridin-3-yl]-1,1-dioxo-1,4-dihydro-1λ$^6$-benzo[1,2,4]thiadiazin-7-yl}methanesulfonamide (67 mg, 38%), as a white solid. $^1$H NMR (400 MHz, CDCl$_3$) δ: 0.81 (t, 6H, J=7.0 Hz), 0.87-1.04 (m, 3H), 1.14 (s, 3H), 1.23-1.56 (m, 4H), 3.06 (s, 3H), 3.15 (q, 2H, J=11.4 Hz), 4.62 (dd, 2H, J$_1$=115.3 Hz, J$_2$=14.7, Hz), 7.03-7.10 (m, 2H), 7.18-7.30 (m, 3H), 7.62-7.71 (m, 2H). LC-MS (ESI) calculated for C$_{26}$H$_{31}$FN$_4$O$_6$S$_2$: 578.6, found 579.2 [M+H$^+$].

Scheme 3 provides a general procedure that can be used to prepare compounds and intermediates of the invention as described by Formula I. Commercially available α,α'-disubstituted β-amino acids (or their salts, such as hydrochlorides), wherein R$^1$ and R$^2$ combine to form a 3- to 6-membered cycloalkyl ring, can be converted to their corresponding β-amino esters, such as methyl esters, using standard conditions, such as (trimethylsilyl)diazomethane. The resulting β-amino esters can then be treated with aldehydes or ketones, where R$^x$ and R$^w$ are independently C$_1$-C$_5$ alkyl, C$_3$-C$_8$ cycloalkyl, —C$_1$-C$_5$ alkylene(C$_3$-C$_8$ cycloalkyl), —C$_1$-C$_5$ alkylene(aryl), —C$_1$-C$_5$ alkylene(heterocyclyl), aryl, or heterocyclyl, or R$^w$ can combine with R$^x$ to form a 3- to 6-membered ring, in the presence of a reducing agent, such as sodium triacetoxyborohydride or sodium cyanoborohydride, to provide N-monoalkylated β-amino esters. Further elucidation of the β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium ethoxide, gives the desired target molecules.

Scheme 3

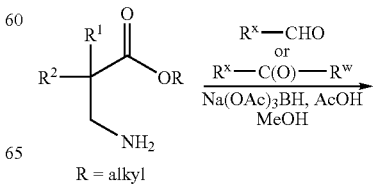

-continued

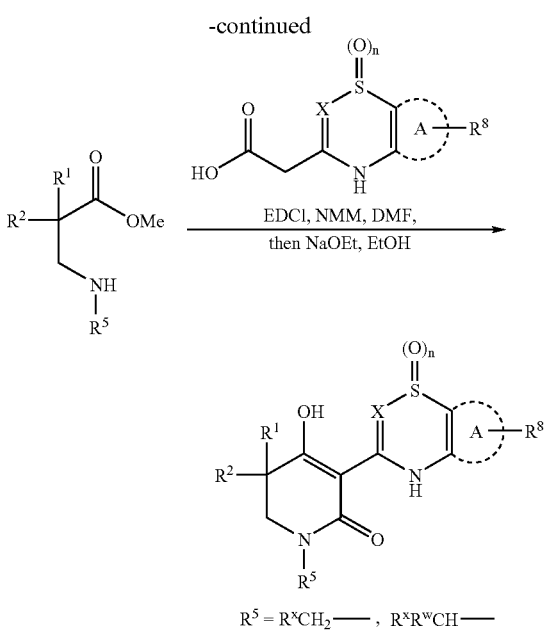

R⁵ = RˣCH₂——, RˣRʷCH——

Example 3

N-{3-[5-(4-Fluoro-benzyl)-8-hydroxy-6-oxo-5-aza-spiro[2.5]oct-7-en-7-yl]-1,1-dioxo-1,4-dihydro-1λ⁶-benzo[1,2,4]thiadiazin-7-yl}-methanesulfonamide

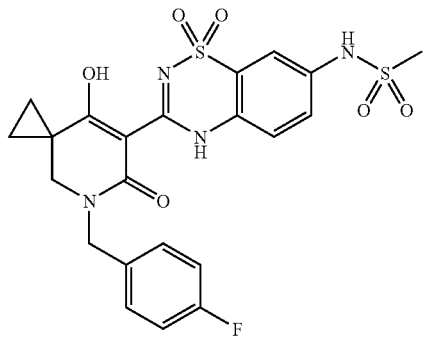

1-[(4-Fluoro-benzylamino)-methyl]-cyclopropanecarboxylic Acid Ethyl Ester

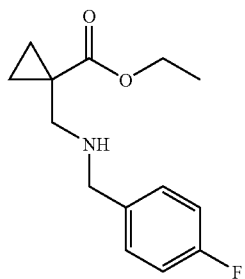

A solution of (1-aminomethyl)-cyclopentyl-acetic acid methyl ester hydrochloride (626 mg, 4.37 mmol) in anhydrous methanol (20 mL) was treated with 4-fluoro-benzaldehyde (0.46 mL, 4.37 mmol) and stirred at 25° C. under a nitrogen environment. After 10 min, glacial acetic acid (0.83 mL, 14.5 mmol) and sodium triacetoxyborohydride (2.3 g, 10.9 mmol) were added sequentially, and the resulting mixture was stirred at 25° C. for 18 h. The reaction was diluted with a saturated aqueous sodium bicarbonate solution (30 mL) and extracted with ethyl acetate (3×50 mL). The combined organic layers were washed with brine (25 mL), dried over sodium sulfate, filtered, and concentrated in vacuo to give 1-[(4-fluoro-benzylamino)-methyl]-cyclopropanecarboxylic acid ethyl ester (870 mg, 79%) as a colorless oil. LC-MS (ESI) calculated for $C_{14}H_{18}FNO_2$: 251.1, found 252.1 [M+H⁺].

b) N-{3-[5-(4-Fluoro-benzyl)-8-hydroxy-6-oxo-5-aza-spiro[2.5]oct-7-en-7-yl]-1,1-dioxo-1,4-dihydro-1λ⁶-benzo[1,2,4]thiadiazin-7-yl}-methanesulfonamide

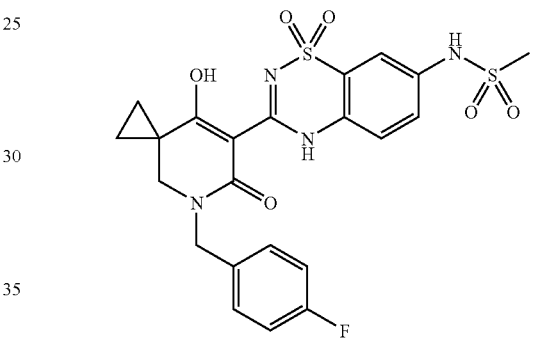

A solution of 1-[(4-fluoro-benzylamino)-methyl]-cyclopropanecarboxylic acid ethyl ester (72 mg, 0.29 mmol) and (7-methanesulfonylamino-1,1-dioxo-1,4-dihydro-1λ⁶-benzo[1,2,4]thiadiazin-3-yl)-acetic acid (105 mg, 0.32 mmol) in anhydrous N,N-dimethylformamide (4 mL) was treated sequentially with N-methylmorpholine (70 µL, 0.64 mmol) and 1-(3-dimethylaminopropyl)-3-ethylcarbodiimide hydrochloride (61 mg, 0.32 mmol). The reaction mixture was stirred at 25° C. for 1 h, diluted with a 1.0 M aqueous hydrochloric acid solution (20 mL), and extracted with ethyl acetate (3×30 mL). The combined organic layers were washed with brine (20 mL), dried over sodium sulfate, filtered, and concentrated in vacuo. The residue was dissolved in ethanol (5 mL), treated with a 21 wt % solution of sodium ethoxide in ethanol (0.5 mL, 1.37 mmol). The reaction was stirred and heated at 60° C. for 1.5 h, allowed to cool to 25° C., and quenched with a 0.5 M aqueous hydrochloric acid solution (10 mL). The resulting mixture was extracted with ethyl acetate (3×30 mL) and the combined organic layers were washed with brine (20 mL), dried over sodium sulfate, filtered, and concentrated in vacuo. The crude residue was purified by prep-HPLC {Column Luna 5µ C18 (2) 100 Å AXIA 150×21.2 mm, 5 micron, 30-100% in 7 min @ 30 mL/min flow rate, 0.05% trifluoroacetic acid in acetonitrile/0.05% trifluoroacetic acid in water} to give N-{3-[5-(4-fluoro-benzyl)-8-hydroxy-6-oxo-5-aza-spiro[2.5]oct-7-en-7-yl]-1,1-dioxo-1,4-dihydro-1λ⁶-benzo[1,2,4]thiadiazin-7-yl}-methanesulfonamide (58 mg, 39%) as a white solid. ¹H NMR (400 MHz, DMSO-d₆) δ: 0.97 (br s, 2H), 1.34 (br s, 2H), 3.06 (s, 3H), 3.41 (s, 2H), 4.65 (s, 2H), 7.17 (t, J=8.8 Hz, 2H), 7.36 (dd, J$_1$=8.8 Hz, J$_2$=5.4 Hz, 2H), 7.51 (dd, J$_1$=8.4 Hz, J$_2$=2.4 Hz, 1H), 7.57-7.60 (m, 2H), 10.16 (s, 1H), 13.86 (br s, 1H). LC-MS (ESI) calculated for C$_{22}$H$_{21}$FN$_4$O$_6$S$_2$: 520.1, found 521.3 [M+H$^+$].

Scheme 4 provides a general procedure that can be used to prepare compounds and intermediates of the invention as described by Formula I. Commercially available β-amino acids (or their salts, such as hydrochlorides), some of which are optically active, can be converted to their corresponding β-amino esters, such as methyl esters, using standard conditions, such as (trimethylsilyl)diazomethane. The resulting β-amino esters can then be treated with aldehydes or ketones, where R$^x$ and R$^w$ are independently C$_1$-C$_5$ alkyl, C$_3$-C$_8$ cycloalkyl, —C$_1$-C$_5$ alkylene(C$_3$-C$_8$ cycloalkyl), —C$_1$-C$_5$ alkylene(aryl), —C$_1$-C$_5$ alkylene(heterocyclyl), aryl, or heterocyclyl, or R$^w$ can combine with R$^x$ to form a 3- to 6-membered ring, in the presence of a reducing agent, such as sodium triacetoxyborohydride or sodium cyanoborohydride, to provide N-monoalkylated β-amino esters. Further elucidation of the β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium ethoxide, gives the desired target molecules.

Scheme 4

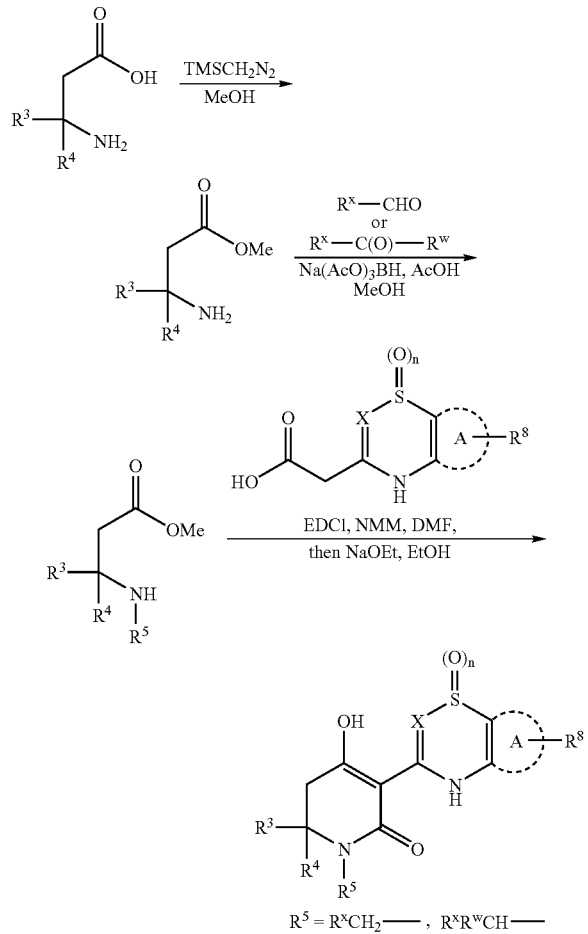

Example 4

N-{3-[6-(4-Fluoro-benzyl)-9-hydroxy-7-oxo-6-azaspiro[4.5]dec-8-en-8-yl]-1,1-dioxo-1,4-dihydro-1λ$^6$-benzo[1,2,4]thiadiazin-7-yl}-methanesulfonamide

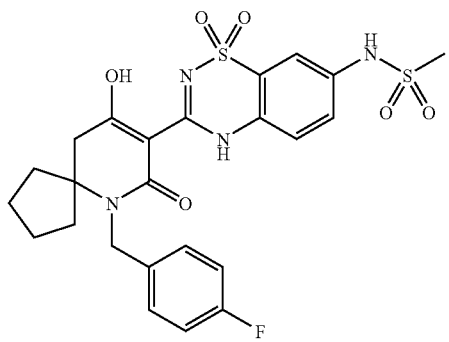

a) (1-Amino-cyclopentyl)-acetic Acid Methyl Ester

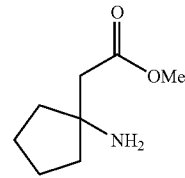

A stirred solution of (1-amino-cyclopentyl)-acetic acid hydrochloride (363 mg, 2.02 mmol) in a 1:1 mixture of anhydrous methanol/benzene (20 mL) cooled to 0° C. under a nitrogen environment was treated dropwise via syringe with a 2.0 M solution of trimethylsilyldiazomethane in toluene (2.0 mL, 4.0 mmol). The reaction mixture was allowed to warm to 25° C., stirred for 1 h, and concentrated in vacuo to give (1-amino-cyclopentyl)-acetic acid methyl ester (311 mg, 98%) as a colorless oil. LC-MS (ESI) calculated for C$_8$H$_{15}$FNO$_2$: 157.2, found 158.2 [M+H$^+$].

[1-(4-Fluoro-benzylamino)-cyclopentyl]-acetic Acid Methyl Ester

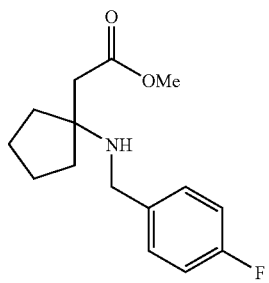

A solution of (1-amino-cyclopentyl)-acetic acid methyl ester (318 mg, 2.02 mmol) in anhydrous methanol (10 mL) was treated with 4-fluoro-benzaldehyde (0.27 mL, 2.56 mmol) and stirred at 25° C. under a nitrogen environment.

After 10 min, glacial acetic acid (0.384 mL, 6.71 mmol) and sodium triacetoxyborohydride (1.1 g, 5.05 mmol) were added sequentially, and the resulting mixture was stirred at 25° C. for 18 h. The reaction was diluted with a saturated aqueous sodium bicarbonate solution (20 mL) and extracted with ethyl acetate (3×20 mL). The combined organic layers were washed with brine (20 mL), dried over sodium sulfate, filtered, and concentrated in vacuo to give [1-(4-fluoro-benzylamino)-cyclopentyl]-acetic acid methyl ester (270 mg, 50%) as a colorless oil. LC-MS (ESI) calculated for $C_{15}H_{20}FNO_2$: 265.3, found 266.2 [M+H$^+$].

c) N-{3-[6-(4-Fluoro-benzyl)-9-hydroxy-7-oxo-6-aza-spiro[4.5]dec-8-en-8-yl]-1,1-dioxo-1,4-dihydro-1$\lambda^6$-benzo[1,2,4]thiadiazin-7-yl}-methanesulfonamide

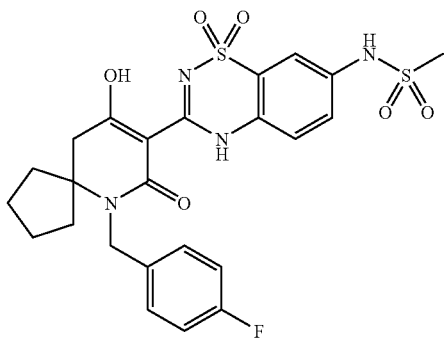

A solution of [1-(4-fluoro-benzylamino)-cyclopentyl]-acetic acid methyl ester (109 mg, 0.41 mmol) and (7-methanesulfonylamino-1,1-dioxo-1,4-dihydro-1$\lambda^6$-benzo[1,2,4]thiadiazin-3-yl)-acetic acid (150 mg, 0.45 mmol) in anhydrous N,N-dimethylformamide (4 mL) was treated sequentially with N-methylmorpholine (100 μL, 0.91 mmol) and 1-(3-dimethylaminopropyl)-3-ethylcarbodiimide hydrochloride (86 mg, 0.45 mmol). The reaction mixture was stirred at 25° C. for 1 h, diluted with a 1.0 M aqueous hydrochloric acid solution (20 mL), and extracted with ethyl acetate (3×40 mL). The combined organic layers were washed with brine (20 mL), dried over magnesium sulfate, filtered, and concentrated in vacuo. The residue was dissolved in ethanol (5 mL), treated with a 21 wt % solution of sodium ethoxide in ethanol (1.0 mL, 2.73 mmol). The reaction was stirred and heated at 60° C. for 1.5 h, allowed to cool to 25° C., and quenched with a 0.5 M aqueous hydrochloric acid solution (10 mL). The resulting mixture was extracted with ethyl acetate (3×40 mL) and the combined organic layers were washed with brine (20 mL), dried over magnesium sulfate, filtered, and concentrated in vacuo. The crude residue was purified by prep-HPLC [Column Luna 5μ C18(2) 100 Å AXIA 150×21.2 mm, 5 micron, 30-100% in 7 min @ 30 mL/min flow rate, 0.05% trifluoroacetic acid in acetonitrile/0.05% trifluoroacetic acid in water] to afford the desired product, N-{3-[6-(4-fluoro-benzyl)-9-hydroxy-7-oxo-6-aza-spiro[4.5]dec-8-en-8-yl]-1,1-dioxo-1,4-dihydro-1$\lambda^6$-benzo[1,2,4]thiadiazin-7-yl}-methanesulfonamide (50 mg, 22%), as an off-white solid. $^1$H NMR (400 MHz, DMSO-d$_6$) δ: 1.55-1.73 (m, 6H), 1.75-1.87 (m, 2H), 2.93 (s, 2H), 3.05 (s, 3H), 4.66 (s, 2H), 7.12 (t, J=8.8 Hz, 2H), 7.34 (dd, J$_1$=8.8 Hz, J$_2$=5.2 Hz, 2H), 7.48 (dd, J$_1$=8.4 Hz, J$_2$=2.4 Hz, 1H), 7.52-7.58 (m, 2H), 10.16 (s, 1H), 13.68 (s, br, 1H). LC-MS (ESI) calculated for $C_{24}H_{25}FN_4O_6S_2$: 548.6, found 549.3 [M+H$^+$].

Scheme 5 provides a general procedure that can be used to prepare compounds and intermediates of the invention as described by Formula I. Commercially available 2-substituted 3-oxo-butyric acid esters can be alkylated with a strong base, such as sodium hydride, and a suitable alkylating agent, such as an alkyl halide. The resulting dialkyl 3-oxo-butyric acid esters can be alkylated with a strong base, such as lithium bis(trimethylsilyl)amide, and a suitable alkylating agent bearing a cyano moiety, such as a cyano alkyl halide, to provide the corresponding nitriles. Reduction of the resulting nitriles via hydrogenation in the presence of a suitable catalyst, such as platinum oxide, provides the cyclic β-amino esters with a 4- to 6-membered heterocyclyl ring. Further elucidation of the cyclic β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium hydride, gives the desired target molecules.

Scheme 5

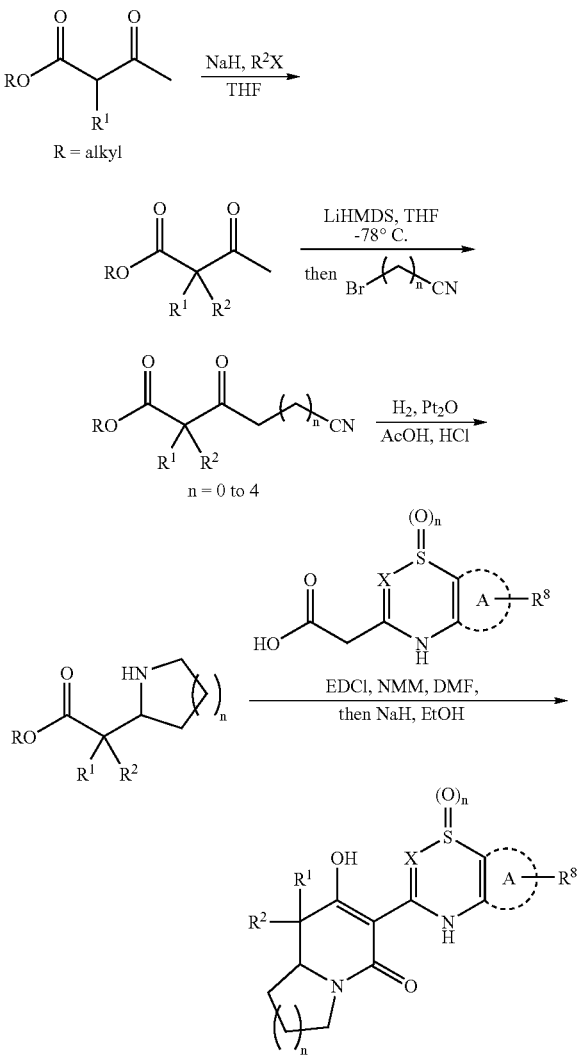

Example 5

N-{3-[7-Hydroxy-8-methyl-8-(3-methyl-butyl)-5-oxo-1,2,3,5,8,8a-hexahydro-indolizin-6-yl]-1,1-dioxo-1,4-dihydro-1λ6-benzo[1,2,4]thiadiazin-7-yl}-methanesulfonamide

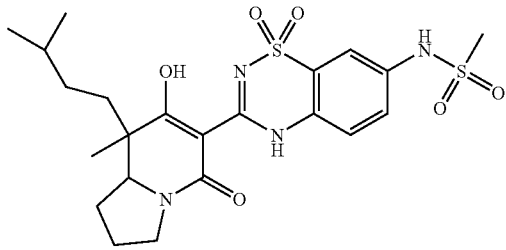

a) 2-Acetyl-2,5-dimethyl-hex-4-enoic Acid Ethyl Ester

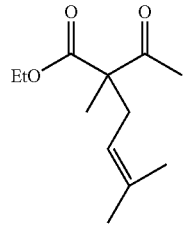

A solution of 2-methyl-3-oxo-butyric acid ethyl ester (3.0 g, 0.0208 mol) in anhydrous N,N-dimethylformamide (80 mL) was cooled to 0° C. and treated with a 60% oil dispersion of sodium hydride (1.0 g, 0.0416 mol). The cooling bath was removed and the reaction mixture was stirred for 10 min. 4-Bromo-2-methyl-2-butene (3.73 g, 0.025 mol) was added and the reaction mixture was stirred for 16 h. The reaction mixture was poured into a mixture of ice and 4.0 M aqueous ammonium chloride solution. The mixture was extracted with ethyl acetate, dried over magnesium sulfate, filtered and concentrated in vacuo. The crude yellow oil was purified by flash column chromatography (ISCO RediSep column, 0 to 15% ethyl acetate in hexanes) to afford the desired product, 2-Acetyl-2,5-dimethyl-hex-4-enoic acid ethyl ester (3.45 g, 78%) as an oil. $^1$H NMR (400 MHz, CDCl$_3$) δ: 1.26 (3H, t, J=7.3 Hz), 1.31 (3H, s), 1.61 (3H, s), 1.69 (3H, s), 2.14 (3H, s), 2.49 (1H, dd, J$_1$=14.8 Hz, J$_2$=7.7 Hz), 2.58 (1H, dd, J$_1$=14.9 Hz, J$_2$=7.5 Hz), 4.18 (2H, q, J=7.3 Hz), 4.92-4.96 (1H, m).

2-(3-Cyano-propionyl)-2,5-dimethyl-hex-4-enoic Acid Ethyl Ester

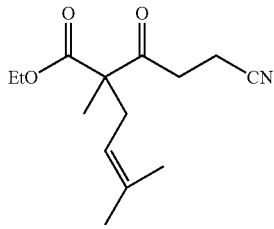

A solution of 2-acetyl-2,5-dimethyl-hex-4-enoic acid ethyl ester (1.0 g, 4.71 mmol) in anhydrous tetrahydro furan (30 mL) was treated with a 1.0 M solution of lithium bis(trimethylsilyl)amide in tetrahydrofuran (5.2 mL, 5.18 mmol) at −78° C. The reaction mixture was stirred at −78° C. for 30 min and was then added via cannula to a solution of bromoacetonitrile (which was stirred for 30 min over basic aluminum oxide, filtered and used fresh in the reaction) in anhydrous tetrahydrofuran (5 mL) cooled to −78° C. The reaction mixture was stirred at −78° C. for 1 h, before it was allowed to warm to 25° C. and quenched by pouring it over ice in a 1.0 M aqueous hydrochloric acid solution. The mixture was extracted with ethyl acetate (3×100 mL), dried over magnesium sulfate, filtered and concentrated in vacuo. Further purification by flash column chromatography (ISCO RediSep column, 0 to 40% ethyl acetate in hexanes) afforded the desired product, 2-(3-cyano-propionyl)-2,5-dimethyl-hex-4-enoic acid ethyl ester (0.71 g, 71%), as an oil. $^1$H NMR (400 MHz, CDCl$_3$) δ: 1.28 (3H, t, J=7.0 Hz), 1.36 (3H, s), 1.63 (3H, s), 1.70 (3H, s), 2.52-2.62 (4H, m), 2.76-2.91 (2H, m), 4.20 (2H, q, J=7.0 Hz), 4.91-4.95 (1H, m). LC-MS (ESI) calcd for C$_{14}$H$_{21}$NO$_3$: 251.15, found 252.3 [M+H$^+$].

2,5-Dimethyl-2-pyrrolidin-2-yl-hexanoic Acid Ethyl Ester

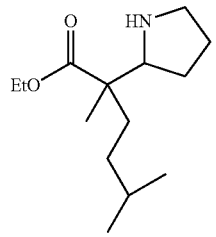

A solution of 2-(3-cyano-propionyl)-2,5-dimethyl-hex-4-enoic acid ethyl ester (323 mg, 1.29 mmol) in acetic acid (20 mL) was treated with one drop of 18.0 M aqueous hydrochloric acid solution and platinum oxide (29 mg, 0.129 mmol). The reaction mixture was degassed and hydrogenated under 50 psi of hydrogen gas for 12 h. The reaction mixture was filtered over celite and the filtrate was concentrated in vacuo. The residue was treated with saturated aqueous sodium bicarbonate solution and extracted with ethyl acetate. The organic layers were dried over magnesium sulfate, filtered and concentrated in vacuo to afford the desired product, 2,5-dimethyl-2-pyrrolidin-2-yl-hexanoic acid ethyl ester (271 mg, 87%) as a light brown oil. This material was directly used in the next step without further purification. $^1$H NMR (400 MHz, CDCl$_3$) δ: 0.87-0.89 (6H, m), 0.97-1.07 (1H, m), 1.13 (3H, s), 1.15-1.22 (1H, m), 1.24-1.29 (3H, m), 1.38-1.57 (3H, m), 1.67-1.81 (4H, m), 2.86-3.00 (2H, m), 3.28-3.36 (1H, m), 4.11-4.18 (2H, m). LC-MS (ESI) calcd for C$_{14}$H$_{27}$NO$_2$: 241.20, found 242.4 [M+H$^+$].

N-{3-[7-Hydroxy-8-methyl-8-(3-methyl-butyl)-5-oxo-1,2,3,5,8,8a-hexahydro-indolizin-6-yl]-1,1-dioxo-1,4-dihydro-1λ6-benzo[1,2,4]thiadiazin-7-yl}-methanesulfonamide

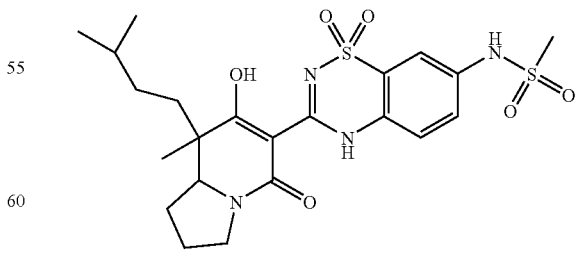

A solution of 2,5-dimethyl-2-pyrrolidin-2-yl-hexanoic acid ethyl ester (266 mg, 1.1 mmol), (7-methanesulfonylamino-1,1-dioxo-1,4-dihydro-1λ6-benzo[1,2,4]thiadiazin-3-yl)-acetic acid (367 mg, 1.1 mmol), and 1-(3-dimethylaminopropyl)-3-ethylcarbodiimide hydrochloride (274 mg, 1.43 mmol) in N,N-dimethylformamide (8 mL) was treated with N-methylmorpholine (289 mg, 2.86 mmol) and stirred for 1 h. The reaction was quenched with 1.0 M aqueous hydrochloric acid solution, extracted with ethyl acetate, dried over magnesium sulfate, filtered and concentrated in vacuo. The crude oil was dissolved in ethanol, treated with a 60% oil dispersion of sodium hydride (176 mg, 7.33 mmol) and heated to a vigorous reflux for 48 h. Upon cooling to 25° C., the reaction mixture was over ice in a 1.0 M aqueous hydrochloride solution. The resulting precipitate was collected by vacuum filtration to afford the crude product as a tan solid. The crude residue was purified by prep-HPLC to afford two separate diastereomers of the desired product, N-{3-[7-hydroxy-8-methyl-8-(3-methyl-butyl)-5-oxo-1,2,3,5,8,8a-hexahydro-indolizin-6-yl]-1,1-dioxo-1,4-dihydro-1$\lambda^6$-benzo[1,2,4]thiadiazin-7-yl}-methanesulfonamide, as tan solids. Assignment of the relative or absolute configuration of the stereocenters was not attempted. Diasteromer 1 (122 mg, 22%): $^1$H NMR (400 MHz, CD$_2$Cl$_2$) δ: 0.84-0.90 (6H, m), 1.27 (3H, s), 1.84-2.20 (2H, m), 3.07 (3H, s), 3.50-3.58 (1H, m), 3.64-3.70 (1H, m), 3.90-3.95 (1H, m), 5.34 (2H, d, J=1.6 Hz), 6.83 (1H, s), 7.25-7.28 (1H, m), 7.54-7.58 (1H, m), 7.66-7.68 (1H, m), 14.22 (1H, s). LC-MS (ESI) calcd for C$_{22}$H$_{30}$N$_4$O$_6$S$_2$ 510.16, found 511.4 [M+H$^+$]. Diasteromer 2 (67 mg, 12%): $^1$H NMR (400 MHz, CD$_2$Cl$_2$) δ: 0.93-0.97 (6H, m), 1.14 (2H, s), 1.22-1.45 (3H, m), 1.52-1.60 (1H, m), 1.83-2.19 (5H, m), 3.06 (3H, s), 3.42-3.59 (1H, m), 3.76-3.96 (2H, m), 5.34 (1H, s), 6.93-6.94 (1H, m), 7.27 (1H, d, J=8.8 Hz), 7.56-7.59 (1H, m), 7.66-7.69 (1H, m), 14.30 (1H, bs), 15.27 (1H, s). LC-MS (ESI) calcd for C$_{22}$H$_{30}$N$_4$O$_6$S$_2$ 510.16, found 511.4 [M+H$^+$].

Scheme 6 provides a general procedure that can be used to prepare compounds and intermediates of the invention as described by Formula I. Commercially available aldehydes can be treated with diazo-acetic acid esters in the presence of a Lewis acid, such as tin (II) chloride, to provide β-ketoesters. In cases where the desired aldehydes are not available, they can be prepared via oxidation of the corresponding alcohols using known methods, such as a Swern oxidation. Treatment of the resulting β-ketoesters with a primary amine gives imines that can undergo subsequent hydrogenation with a reducing agent, such as sodium cyanoborohydride, to provide N-monoalkylated β-amino esters. Further elucidation of the β-amino esters can be achieved through coupling with an acid intermediate using standard peptide coupling reagents, such as 1-(3-dimethylaminopropyl)-3-ethylcarbodiimide hydrochloride, to afford the corresponding amides. Treatment of the resulting amides with a base, such as sodium hydride, gives the desired target molecules.

Scheme 6

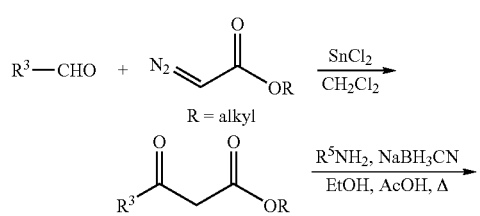

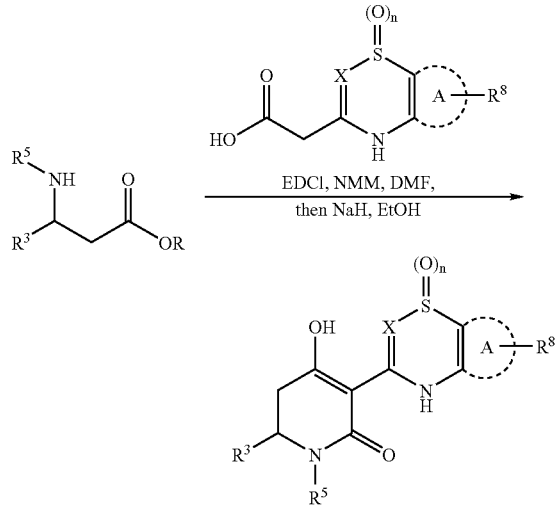

Example 6

N-{3-[1-(4-Fluoro-benzyl)-4-hydroxy-6-(3-methyl-butyl)-2-oxo-1,2,5,6-tetrahydro-pyridin-3-yl]-1,1-dioxo-1,2-dihydro-1$\lambda^6$-benzo[1,2,4]thiadiazin-7-yl}-methanesulfonamide

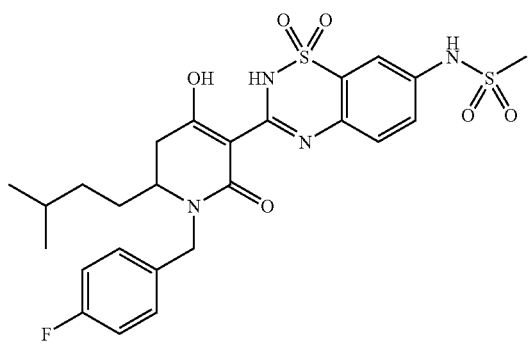

a) 4-Methyl-pentanal

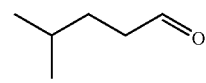

A 2.0 M solution of oxalylchloride in dichloromethane (26.91 mL, 53.83 mmol) in dichloromethane (250 mL) was stirred at −78° C. under a blanket of nitrogen and treated dropwise via syringe with dimethyl sulfoxide (7.65 mL, 107.65 mmol) over 30 min. The reaction was treated with a solution of 4-methyl-pentan-1-ol (5.0 g, 48.93 mmol) in dichloromethane (150 mL) via a dropping funnel over 1 h, making sure the temperature never exceeded −60° C., then allowed to stir for 3 h at −78° C. Triethylamine (34.39 mL, 244.67 mmol) was added to the reaction and the reaction was allowed to warm to 25° C. The reaction was treated with deionized water (300 mL) and dichloromethane (300 mL) and the layers were separated. The organic layer was extracted with aqueous saturated brine solution, dried over sodium sulfate, filtered and concentrated in vacuo. The crude material was purified by flash column chromatography (ISCO RediSep column, 0 to 30% ethyl acetate in hexanes) to afford the desired product, 4-methyl-pentanal (464 mg, 9.5%), as a light yellow oil. $^1$H NMR (400 MHz, CDCl$_3$) δ: 0.91 (6H, d, J=6.3 Hz), 1.25-1.34 (1H, m), 1.49-1.55 (2H, m), 2.40-2.44 (2H, m), 9.74 (1H, t, J=2.0 Hz).

b) 6-Methyl-3-oxo-heptanoic Acid Ethyl Ester

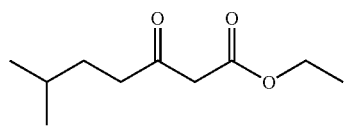

A solution of diazo-acetic acid ethyl ester (555 mg, 4.86 mmol) in dichloromethane (8 mL) was treated with tin (II) chloride (88 mg, 0.463 mmol) and stirred vigorously at 25° C. A solution of 4-methyl-pentanal (464 mg, 4.63 mmol) in dichloromethane (2 mL) was added to the mixture dropwise over 10 min resulting in gas evolution. After the nitrogen evolution ceased (approximately 1 h), the reaction was extracted with brine and diethyl ether (2×80 mL). The organic layers were combined, dried over sodium sulfate, filtered and concentrated in vacuo. The crude material was purified by flash column chromatography (ISCO RediSep column, 0 to 7% ethyl acetate in hexanes) to afford the desired product, 6-methyl-3-oxo-heptanoic acid ethyl ester (478 mg, 55%), as a light yellow oil. $^1$H NMR (400 MHz, CDCl$_3$) δ: 0.89 (6H, d, J=6.3 Hz), 1.26-1.29 (4H, m), 1.48-1.57 (2H, m), 2.53 (2H, t, J=7.4 Hz), 3.42 (2H, s), 4.18 (2H, quartet, J=7.6 Hz).

c) 3-(4-Fluoro-benzylamino)-6-methyl-heptanoic Acid Ethyl Ester

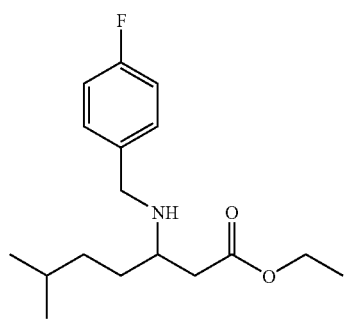

A solution of 3-(4-fluoro-benzylamino)-6-methyl-heptanoic acid ethyl ester (126 mg, 0.677 mmol) in ethanol (30 mL) was treated with 4-fluorobenzylamine (93 mg, 0.744 mmol), sodium cyanoborohydride (94 mg, 1.49 mmol), a couple drops of acetic acid and molecular sieves (4 Å, powder, 30 mg) and was stirred at 50° C. for 18 h. The reaction was allowed to cool to 25° C., treated with 6.0 M aqueous hydrochloric acid solution (5 mL) and stirred for 30 min at 25° C. Water (50 mL) was added to the reaction mixture along with solid potassium carbonate until pH 10 was reached. The mixture was then extracted with ethyl acetate (3×50 mL). The organic layers were combined, dried over sodium sulfate and concentrated in vacuo. The crude material was purified by flash column chromatography (ISCO RediSep column, 0 to 80% ethyl acetate in hexanes) to afford the desired product, 3-(4-fluoro-benzylamino)-6-methyl-heptanoic acid ethyl ester (93 mg, 47%) as a clear oil. LC-MS calculated for C$_{17}$H$_{26}$FNO$_2$: 295.2, found 296.4 [M+H$^+$].

d) N-{3-[1-(4-Fluoro-benzyl)-4-hydroxy-6-(3-methyl-butyl)-2-oxo-1,2,5,6-tetrahydro-pyridin-3-yl]-1,1-dioxo-1,2-dihydro-1λ$^6$-benzo[1,2,4]thiadiazin-7-yl}-methanesulfonamide

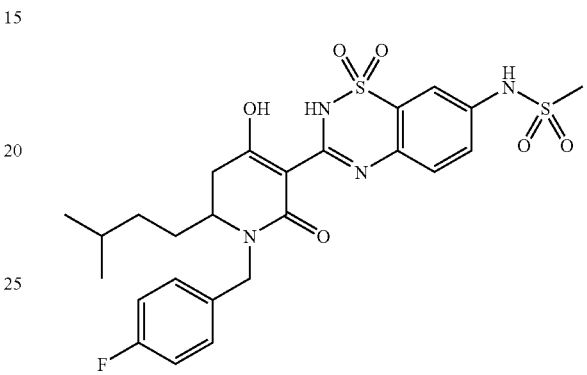

A solution of 3-(4-fluoro-benzylamino)-6-methyl-heptanoic acid ethyl ester (93 mg, 0.315 mmol), (7-methanesulfonylamino-1,1-dioxo-1,4-dihydro-1λ$^6$-benzo[1,2,4]thiadiazin-3-yl)-acetic acid (105 mg, 0.315 mmol), and 1-(3-dimethylaminopropyl)-3-ethylcarbodiimide hydrochloride (73 mg, 0.378 mmol) in anhydrous N,N-dimethyformamide (4 mL) was treated with N-methyl morpholine (0.083 mL, 0.756 mmol). The reaction was stirred under a nitrogen environment at 50° C. for 18 h, quenched with a 6.0 M aqueous hydrochloric acid solution (50 mL), extracted with ethyl acetate (2×50 mL), dried over sodium sulfate, filtered, and concentrated in vacuo. The resulting oil was dissolved in ethanol (5 mL) and treated with sodium ethoxide (470 µL, 21% w/w, 1.26 mmol). The reaction was heated at 60° C. under a nitrogen environment for 18 h. The reaction mixture was allowed to cool to 25° C., quenched with a 1.0 M aqueous hydrochloric acid solution (50 mL), extracted with ethyl acetate (2×50 mL), washed with brine (50 mL), dried with sodium sulfate, filtered, and concentrated in vacuo. The crude resin was purified by flash column chromatography (ISCO RediSep column, 0 to 80% ethyl acetate in hexanes) to afford the desired product, N-{3-[1-(4-fluoro-benzyl)-4-hydroxy-6-(3-methyl-butyl)-2-oxo-1,2,5,6-tetrahydro-pyridin-3-yl]-1,1-dioxo-1,2-dihydro-1λ$^6$-benzo[1,2,4]thiadiazin-7-yl}-methanesulfonamide (63.6 mg, 36%) as a white powder. $^1$H NMR (400 MHz, CDCl$_3$) δ: 0.90 (6H, d, J=6.9 Hz), 1.08-1.27 (2H, m), 1.50-1.75 (3H, m), 2.60 (1H, d, J=17.3 Hz), 2.95-3.01 (1H, m), 3.06 (3H, s), 3.37-3.49 (1H, m), 3.98 (1H, d, J=14.9 Hz), 5.30 (1H, d, J=15.0 Hz), 7.03-7.08 (2H, m), 7.20-7.28 (3H, m), 7.46 (1H, bs), 7.65-7.67 (1H, m), 7.71-7.73 (1H, m). LC-MS calculated for C$_{25}$H$_{29}$FN$_4$O$_6$S$_2$: 564.2, found 565.5 [M+H$^+$].

By repeating the procedures described in the above examples, and using appropriate starting materials, the following compounds of Formula I as identified in Table I, were obtained. All products conformed by LC-MS (ESI) analysis and showed the desired mass as [M+H$^+$].

TABLE 1

| Example | Structure | Spectral data | NS5B Polymerase IC50 |
|---------|-----------|---------------|----------------------|
| 1 | 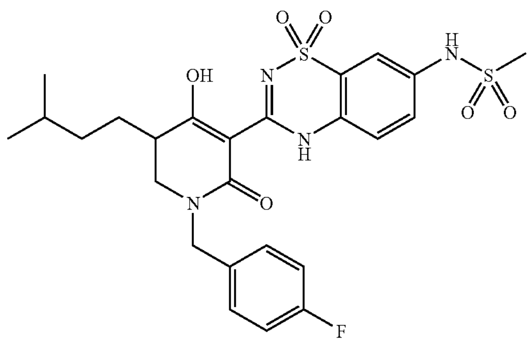 | $^1$H NMR (400 MHz, CDCl$_3$) δ: 0.78-0.83 (m, 6H), 0.95-1.12 (m, 2H), 1.31-1.45 (m, 2H), 1.64-1.73 (m, 1H), 2.50-2.55 (m, 1H), 3.06 (s, 3H), 3.18 (dd, 1H, J$_1$ = 12.7 Hz, J$_2$ = 4.3 Hz), 3.52 (dd, 1H, J$_1$ = 12.9 Hz, J$_2$ = 5.0 Hz), 4.31 (d, 1H, J = 14.9 Hz), 4.93 (d, 1H, J = 14.7 Hz), 6.84 (bs, 1H), 7.06 (t, 2H, J = 8.6 Hz), 7.23-7.29 (m, 3H), 7.64 (dd, 1H, J$_1$ = 8.7 Hz, J$_2$ = 2.3 Hz), 7.68 (d, 1H, J = 2.3 Hz). | ++ |
| 2 | 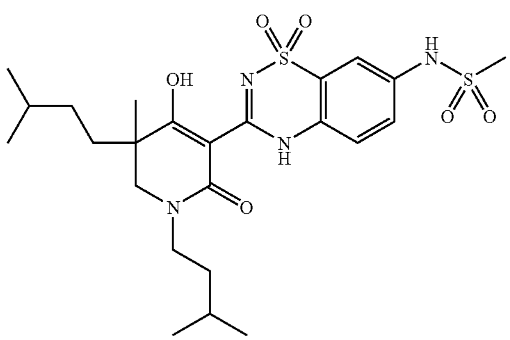 | $^1$H NMR (400 MHz, CDCl$_3$) δ: 0.90-0.92 (m, 6H), 0.99 (d, 6H, J = 5.9 Hz), 1.14 (s, 1H), 1.17-1.27 (m, 5H), 1.47-1.67 (m, 8H), 3.05 (d, 3H, J = 5.4 Hz), 3.17-3.29 (m, 2H), 3.44-3.54 (m, 2H), 7.17-7.24 (m, 1H), 7.59-7.67 (m, 2H). | ++ |
| 3 | 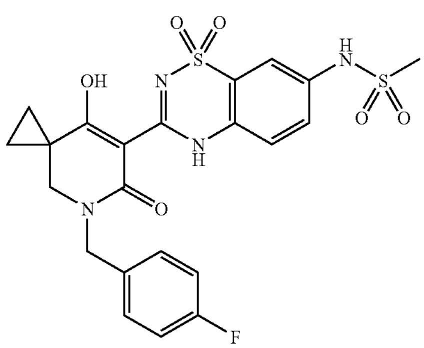 | $^1$H NMR (DMSO-d$_6$, 400 MHz) δ: 0.97 (s, br, 2H), 1.34 (s, br, 2H), 3.06 (s, 3H), 3.41 (s, 2H), 4.65 (s, 2H), 7.17 (t, J = 8.8 Hz, 2H), 7.36 (dd, J$_1$ = 8.8 Hz, J$_2$ = 5.4 Hz, 2H), 7.51 (dd, J$_1$ = 8.4 Hz, J$_2$ = 2.4 Hz, 1H), 7.57-7.60 (m, 2H), 10.16 (s, 1H), 13.86 (s, br, 1H). | +++ |
| 4 | 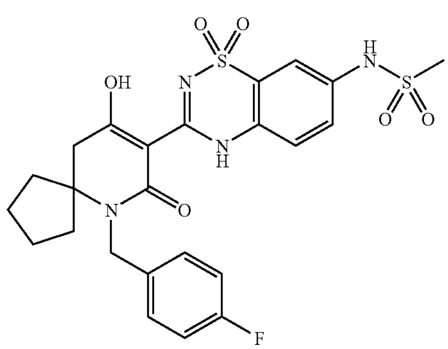 | $^1$H NMR (DMSO-d$_6$, 400 MHz) δ: 1.55-1.73 (m, 6H), 1.75-1.87 (m, 2H), 2.93 (s, 2H), 3.05 (s, 3H), 4.66 (s, 2H), 7.12 (t, J = 8.8 Hz, 2H), 7.34 (dd, J1 = 8.8 Hz, J2 = 5.2 Hz, 2H), 7.48 (dd, J1 = 8.4 Hz, J2 = 2.4 Hz, 1H), 7.52-7.58 (m, 2H), 10.16 (s, 1H), 13.68 (s, br, 1H). | +++ |

TABLE 1-continued

| Example | Structure | Spectral data | NS5B Polymerase IC50 |
|---|---|---|---|
| 5 | 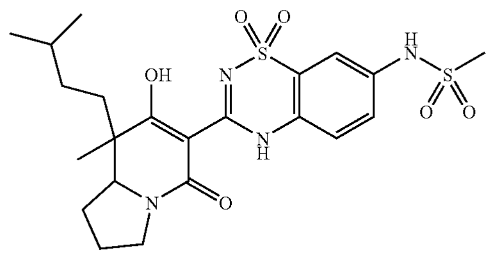 | ¹H NMR (400 MHz, CD₂Cl₂) δ: 0.84-0.90 (6H, m), 1.27 (3H, s), 1.84-2.20 (2H, m), 3.07 (3H, s), 3.50-3.58 (1H, m), 3.64-3.70 (1H, m), 3.90-3.95 (1H, m), 5.34 (2H, d, J = 1.6 Hz), 6.83 (1H, s), 7.25-7.28 (1H, m), 7.54-7.58 (1H, m), 7.66-7.68 (1H, m), 14.22 (1H, s).<br><br>¹H NMR (400 MHz, CD₂Cl₂) δ: 0.93-0.97 (6H, m), 1.14 (2H, s), 1.22-1.45 (3H, m), 1.52-1.60 (1H, m), 1.83-2.19 (5H, m), 3.06 (3H, s), 3.42-3.59 (1H, m), 3.76-3.96 (2H, m), 5.34 (1H, s), 6.93-6.94 (1H, m), 7.27 (1H, d, J = 8.8 Hz), 7.56-7.59 (1H, m), 7.66-7.69 (1H, m), 14.30 (1H, bs), 15.27 (1H, s). | +++ |
| 6 | 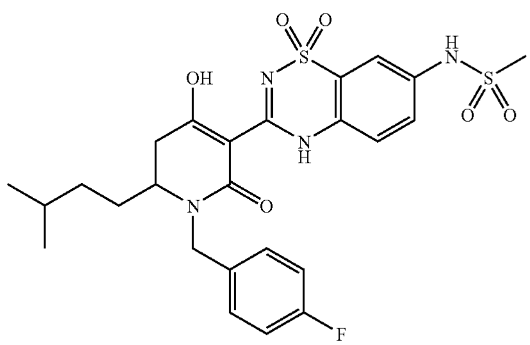 | ¹H NMR (400 MHz, CDCl₃) δ: 0.90 (6H, d, J = 6.9 Hz), 1.08-1.27 (2H, m), 1.50-1.75 (3H, m), 2.60 (1H, d, J = 17.3 Hz), 2.95-3.01 (1H, m), 3.06 (3H, s), 3.37-3.49 (1H, m), 3.98 (1H, d, J = 14.9 Hz), 5.30 (1H, d, J = 15.0 Hz), 7.03-7.08 (2H, m), 7.20-7.28 (3H, m), 7.46 (1H, bs), 7.65-7.67 (1H, m), 7.71-7.73 (1H, m). | ++ |
| 7 | 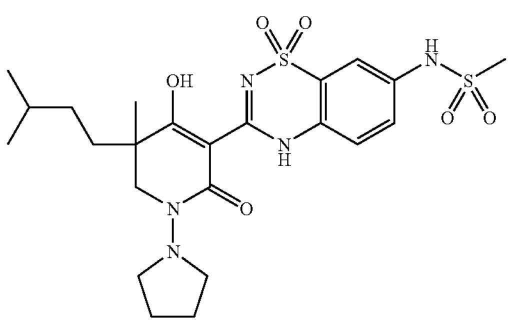 | Prepared as described in Example 2.<br>¹H NMR (400 MHz, CD₂Cl₂) δ: 1.43 (d, 6H, J = 7.3 Hz), 1.75-1.79 (m, 4H), 2.00-2.12 (m, 2H), 2.17-2.21 (m, 2H), 2.40 (bs, 4H), 3.56 (s, 3H), 3.65 (bs, 4H), 3.87 (d, 1H, J = 12.3 Hz), 3.95 (d, 1H, J = 13.1 Hz), 7.65 (s, 1H), 7.77 (d, 1H, J = 8.5 Hz), 8.09 (dd, 1H, J₁ = 8.4 Hz, J₂ = 2.4 Hz), 8.20 (d, 1H, J = 2.2 Hz). | +++ |
| 8 | 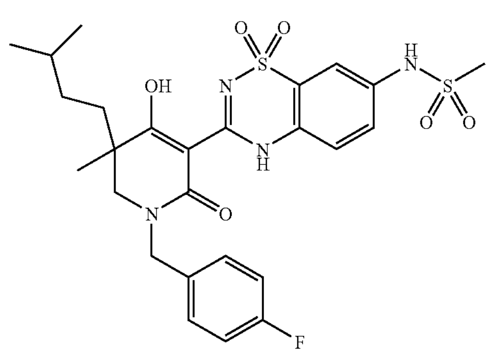 | Prepared as described in Example 2.<br>¹H NMR (400 MHz, CDCl₃) δ: 0.90-0.92 (m, 6H), 0.99 (d, 6H, J = 5.9 Hz), 1.14 (s, 1H), 1.17-1.27 (m, 5H), 1.47-1.67 (m, 8H), 3.05 (d, 3H, J = 5.4 Hz), 3.17-3.29 (m, 2H), 3.44-3.54 (m, 2H), 7.17-7.24 (m, 1H), 7.59-7.67 (m, 2H). | ++ |

TABLE 1-continued

| Example | Structure | Spectral data | NS5B Polymerase IC50 |
|---|---|---|---|
| 9 | 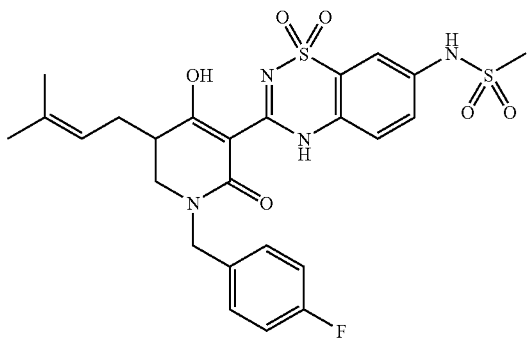 | Prepared as described in Example 1. ¹H NMR (400 MHz, CDCl₃) δ: 1.54 (s, 3H), 1.69 (s, 3H), 2.15-2.23 (m, 1H), 2.39-2.44 (m, 1H), 2.60-2.66 (m, 1H), 3.06 (s, 3H), 3.19 (dd, 1H, J₁ = 13.1 Hz, J₂ = 4.3 Hz), 3.45 (dd, 1H, J₁ = 12.4 Hz, J₂ = 5.4 Hz), 4.61 (s, 2H), 4.89 (t, 3H, J = 6.6 Hz), 7.05 (t, 2H, J = 8.5 Hz), 7.23-7.28 (m, 3H), 7.63-7.66 (m, 1H), 7.69 (d, 1H, J = 2.2 Hz). | ++ |
| 10 | 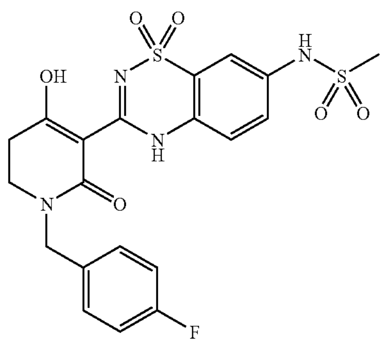 | Prepared as described in Example 3. ¹H NMR (400 MHz, Acetone-d₆) δ: 2.91 (t, 2H, J = 7.0 Hz), 3.11 (s, 3H), 3.60 (t, 2H, J = 7.3 Hz), 4.75 (bs, 2H), 7.10-7.14 (m, 2H), 7.43-7.46 (m, 2H), 7.57 (d, 1H, J = 8.4 Hz), 7.71 (dd, 1H, J₁ = 8.6 Hz, J₂ = 2.5 Hz), 7.81 (d, 1H, J = 2.5 Hz), 8.96 (bs, 1H). | ++ |
| 11 | 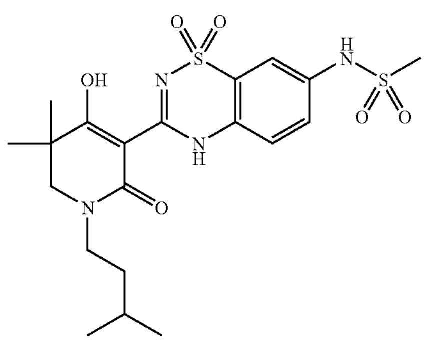 | Prepared as described in Example 2. ¹H NMR (400 MHz, CDCl₃) δ: 0.99 (d, 6H, J = 6.2 Hz), 1.29 (s, 6H), 1.45-1.69 (m, 5H), 3.06 (s, 3H), 3.20 (s, 2H), 3.48 (t, 2H, J = 7.8 Hz), 6.92 (bs, 1H), 7.23 (d, 1H, J = 8.5 Hz), 7.60-7.65 (m, 1H), 7.66-7.68 (m, 1H). | ++ |
| 12 | 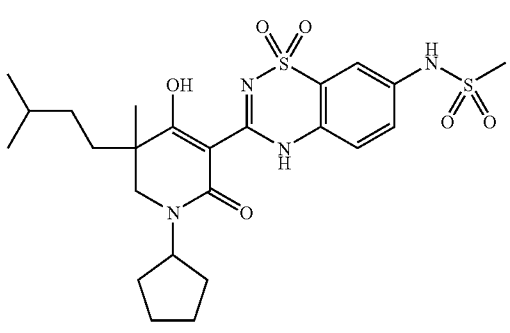 | Prepared as described in Example 2. ¹H NMR (400 MHz, CDCl₃) δ: 0.91 (d, 6H, J = 6.2 Hz), 1.17-1.21 (m, 2H), 1.23 (s, 3H), 1.50-1.99 (m, 13H), 3.06 (s, 3H), 3.14-3.27 (m, 2H), 5.00 (quintet, 1H, J = 8.6 Hz), 6.76 (bs, 1H), 7.18-7.21 (m, 1H), 7.60-7.64 (m, 1H), 7.66-7.67 (m, 1H). | +++ |

TABLE 1-continued

| Example | Structure | Spectral data | NS5B Polymerase IC50 |
|---|---|---|---|
| 13 | 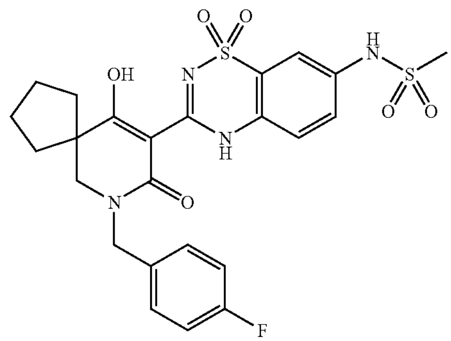 | Prepared as described in Example 3.<br>$^1$H NMR (400 MHz, DMSO-d$_6$) δ: 1.70-1.40 (m, 6H), 1.87 (m, 2H), 3.06 (s, 3H), 3.32 (s, 2H), 4.66 (s, 2H), 7.18 (t, 2H, J = 8.8 Hz), 7.41 (m, 2H), 7.52 (m, 1H), 7.60 (m, 2H), 10.17 (s, 1H). | +++ |
| 14 | 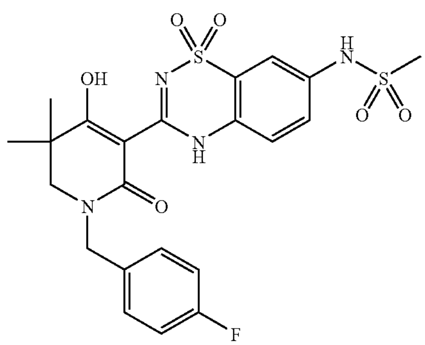 | Prepared as described in Example 2.<br>$^1$H NMR (400 MHz, CDCl$_3$) δ: 1.08 (s, 1H), 1.18 (s, 6H), 1.59 (bs, 1H), 3.07 (s, 3H), 3.12 (s, 2H), 4.64 (s, 2H), 7.03-7.11 (m, 2H), 7.17-7.33 (m, 3H), 7.60-7.69 (m, 2H). | +++ |
| 15 | 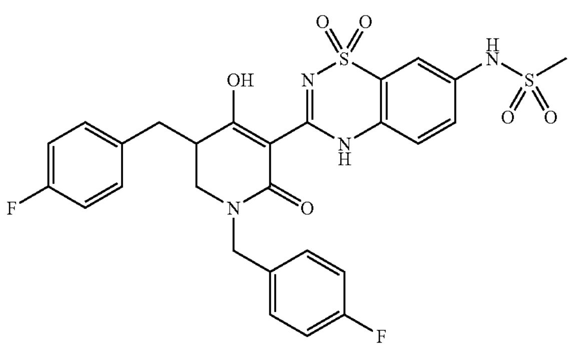 | Prepared as described in Example 1.<br>$^1$H NMR (400 MHz, Acetone-d$_6$) δ: 2.71-2.73 (m, 1H), 3.03-3.06 (m, 1H), 3.12 (s, 3H), 3.15 (bs, 1H), 3.22-3.24 (m, 1H), 3.58-3.62 (m, 1H), 4.50-4.53 (m, 1H), 4.85-4.88 (m, 1H), 5.62 (s, 1H), 6.97-7.07 (m, 4H), 7.13-7.18 (m, 2H), 7.42-7.46 (m, 2H), 7.58-7.60 (m, 1H), 7.72 (d, 1H, J = 8.5 Hz), 7.82 (d, 1H, J = 1.5 Hz), 8.00 (s, 1H), 8.97 (bs, 1H). | ++ |
| 16 | 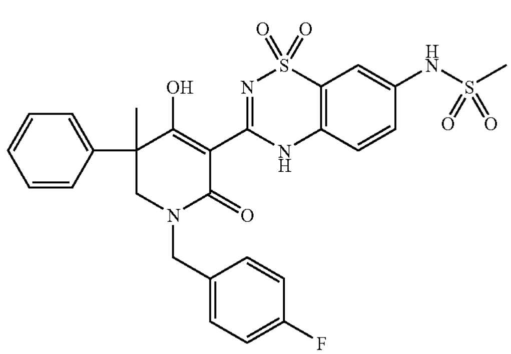 | Prepared as described in Example 2.<br>$^1$H NMR (400 MHz, CDCl$_3$) δ: 1.55 (s, 3H), 1.70 (bs, 1H), 3.08 (s, 3H), 3.49-3.59 (m, 2H), 4.42-4.68 (m, 2H), 6.88-6.93 (m, 2H), 6.97-7.02 (m, 2H), 7.05-7.15 (m, 3H), 7.22-7.27 (m, 3H), 7.63-7.71 (m, 2H). | + |

TABLE 1-continued

| Example | Structure | Spectral data | NS5B Polymerase IC50 |
|---|---|---|---|
| 17 | 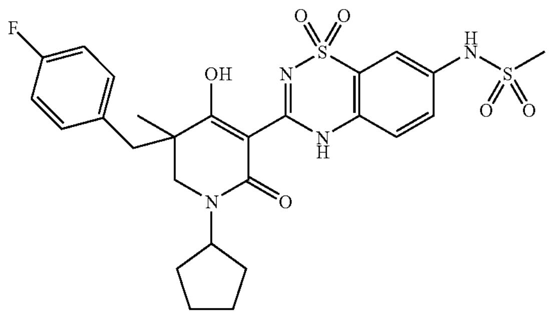 | Prepared as described in Example 2.<br>$^{1}$H NMR (400 MHz, CDCl$_3$) δ: 1.20 (d, 3H, J = 41.6 Hz), 1.46-1.77 (m, 6H), 1.85-1.97 (m, 2H), 2.19-2.27 (m, 2H), 2.87-3.01 (m, 3H), 3.07 (d, 3H, J = 3.1 Hz), 3.18-3.26 (m, 1H), 4.76-4.96 (m, 1H), 6.84 (d, 1H, J = 8.7 Hz), 7.01 (t, 2H, J = 8.6 Hz), 7.06-7.13 (m, 2H), 7.22 (q, 1H, J = 5.2 Hz), 7.63-7.66 (m, 1H), 7.68-7.69 (m, 1H). | + |
| 18 | 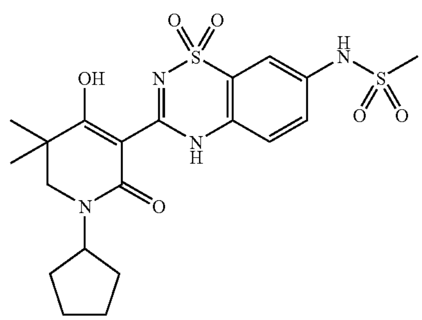 | Prepared as described in Example 2.<br>$^{1}$HNMR (400 MHz, DMSO-d$_6$) δ: 1.14-1.25 (6H, m), 1.58-1.72 (6H, m), 3.06 (3H, s), 3.23-3.33 (4H, m), 4.75-4.97 (1H, m), 7.50-7.57 (3H, m), 10.16 (1H, bs). | + |
| 19 | 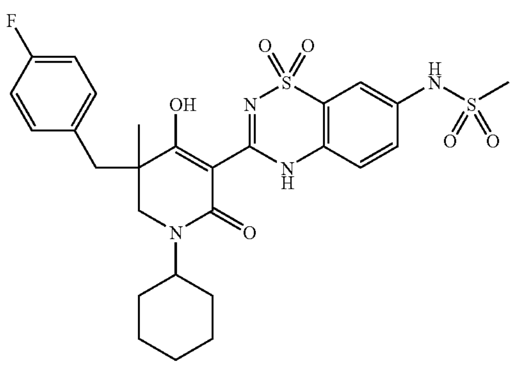 | Prepared as described in Example 2.<br>$^{1}$H NMR (400 MHz, CDCl$_3$) δ: 1.19 (d, 3H, J = 40.8 Hz), 1.27-1.51 (m, 5H), 1.67-1.88 (m, 5H),, 2.86-2.96 (m, 2H), 3.01-3.13 (m, 1H), 3.07 (d, 3H, J = 3.9 Hz), 3.19-3.27 (m, 1H), 4.34-4.51 (m, 1H), 6.96-7.03 (m, 2H), 7.06-7.13 (m, 2H), 7.21 (t, 1H, J = 9.0 Hz), 7.63-7.67 (m, 1H), 7.70-7.70 (m, 1H). | + |
| 20 | 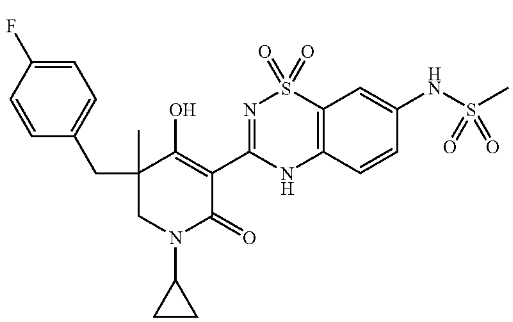 | Prepared as described in Example 2.<br>$^{1}$H NMR (400 MHz, CDCl$_3$) δ: 0.65-0.83 (m, 2H), 0.91-1.08 (m, 2H), 1.24 (d, 3H, J = 44.3 Hz), 2.77-2.83 (m, 1H), 2.87-2.96 (m, 1H), 3.00-3.08 (m, 1H), 3.13 (d, 3H, J = 4.6 Hz), 3.15-3.22 (m, 1H), 3.34-3.43 (m, 1H), 7.03-7.18 (m, 4H), 7.28-7.32 (m, 1H), 7.71-7.73 (m, 1H), 7.76-7.78 (m, 1H). | ++ |

TABLE 1-continued

| Example | Structure | Spectral data | NS5B Polymerase IC50 |
|---|---|---|---|
| 21 | 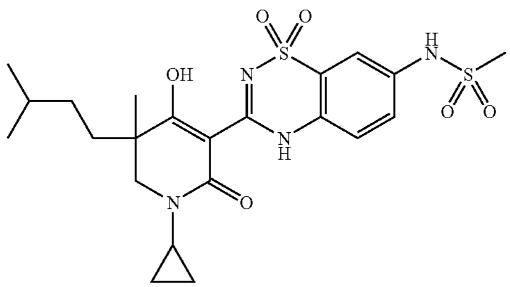 | Prepared as described in Example 2. $^1$H NMR (400 MHz, CDCl$_3$) δ: 0.70-0.71 (m, 2H), 0.91 (d, 6H, J = 6.2 Hz), 0.95-1.04 (m, 2H), 1.13-1.26 (m, 2H), 1.20 (s, 3H), 1.47-1.54 (m, 1H), 1.56-1.61 (m, 2H), 2.73 (septet, 1H, J = 3.6 Hz), 3.04 (s, 3H), 3.26 (dd, 2H, J$_1$ = 47.3 Hz, J$_2$ = 12.8 Hz), 7.00 (bs, 1H), 7.17-7.25 (m, 1H), 7.61-7.65 (m, 1H), 7.67-7.69 (m, 1H). | +++ |
| 22 | 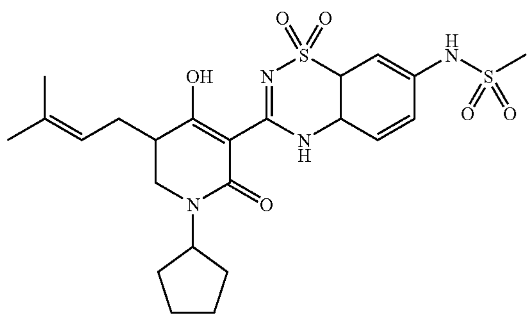 | Prepared as described in Example 1. $^1$H NMR (400 MHz, CDCl$_3$) δ: 1.46-1.61 (m, 2H), 1.64 (s, 3H), 1.67-1.73 (m, 2H), 1.76 (s, 3H), 1.83-1.99 (m, 2H), 2.25-2.33 (m, 1H), 2.45-2.52 (m, 1H), 2.66 (sextet, 1H, J = 4.8 Hz), 3.06 (s, 3H), 3.20 (dd, 1H, J$_1$ = 12.4 Hz, J$_2$ = 7.3 Hz), 3.38-3.42 (m, 1H), 3.40 (dd, 1H, J$_1$ = 12.9 Hz, J$_2$ = 5.1 Hz), 4.91-4.99 (m, 1H), 5.08-5.11 (m, 1H), 7.06 (s, 1H), 7.18-7.21 (m, 1H), 7.62-7.66 (m, 1H), 7.68-7.70 (m, 1H). | +++ |
| 23 | 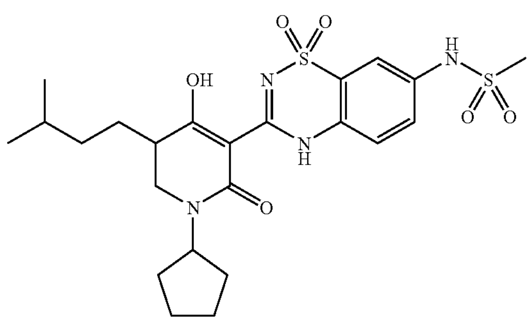 | Prepared as described in Example 1. $^1$H NMR (400 MHz, CDCl$_3$) δ: 0.92 (d, 3H, J = 3.1 Hz), 0.93 (d, 3H, J = 3.1 Hz), 1.25-1.35 (m, 2H), 1.43-2.00 (m, 11H), 2.56 (sextet, 1H, J = 4.5 Hz), 3.05 (s, 3H), 3.19 (dd, 1H, J$_1$ = 12.9 Hz, J$_2$ = 4.2 Hz), 3.45 (dd, 1H, J$_1$ = 13.1 Hz, J$_2$ = 4.7 Hz), 4.98 (quintet, 1H, J = 8.6 Hz), 7.01 (s, 1H), 7.19 (d, 1H, J = 9.2 Hz), 7.61-7.65 (m, 1H), 7.67-7.69 (m, 1H). | +++ |
| 24 | 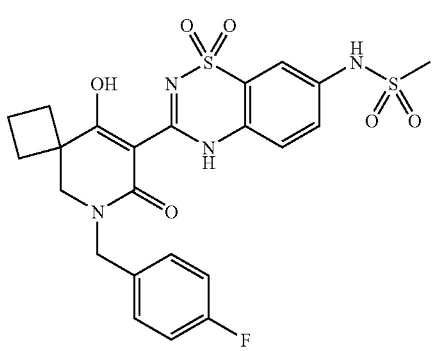 | Prepared as described in Example 3. $^1$H NMR (400 MHz, CDCl$_3$) δ: 1.27 (bs, 2H), 1.71-1.78 (m, 2H), 1.84-2.08 (m, 2H), 2.40-2.58 (m, 2H), 3.07 (s, 3H), 3.41 (s, 2H), 4.65 (s, 2H), 7.05-7.12 (m, 2H), 7.20-7.33 (m, 3H), 7.62-7.67 (m, 1H), 7.69-7.71 (m, 1H). | +++ |

TABLE 1-continued

| Example | Structure | Spectral data | NS5B Polymerase IC50 |
| --- | --- | --- | --- |
| 25 | 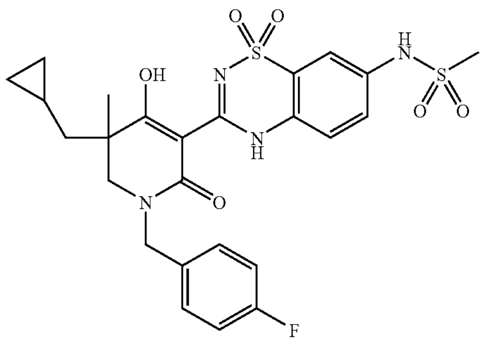 | Prepared as described in Example 2.<br>$^1$H NMR (400 MHz, CDCl$_3$) δ: 0.46-0.48 (m, 2H), 0.94-1.01 (m, 3H), 1.71 (s, 3H), 1.90-2.06 (m, 2H), 3.55 (s, 3H), 3.74 (dd, 2H, J$_1$ = 51.6 Hz, J$_2$ = 13.2 Hz), 5.13 (dd, 2H, J$_1$ = 79.1 Hz, J$_2$ = 14.5 Hz), 7.44-7.59 (m, 2H), 7.72-7.82 (m, 3H), 8.10-8.18 (m, 2H). | +++ |
| 26 | 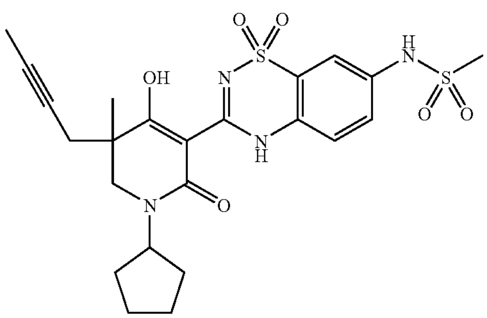 | Prepared as described in Example 2.<br>$^1$H NMR (400 MHz, CDCl$_3$) δ: 1.31 (s, 3H), 1.52-1.99 (m, 11H), 2.41-2.53 (m, 2H), 3.05 (s, 3H), 3.12 (d, 1H, J = 13.3 Hz), 3.42 (d, 1H, J = 12.3 Hz), 5.01 (quintet, 1H, J = 8.2 Hz), 7.13 (s, 1H), 7.18 (t, 1H, J = 8.6 Hz), 7.61-7.66 (m, 1H), 7.68-7.69 (m, 1H). | ++ |
| 27 | 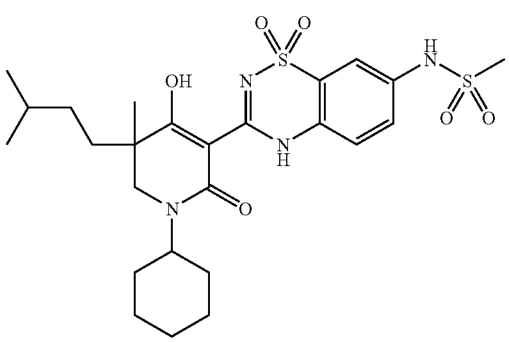 | Prepared as described in Example 2.<br>$^1$H NMR (400 MHz, CDCl$_3$) δ: 0.91 (d, 6H, J = 6.2 Hz), 1.10-1.27 (m, 4H), 1.22 (s, 3H), 1.43-1.66 (m, 8H), 1.72-1.80 (m, 3H), 1.88-1.90 (m, 2H), 3.06 (s, 3H), 3.09-3.31 (m, 2H), 4.47-4.53 (m, 1H), 7.01 (d, 1H, J = 4.0 Hz), 7.17-7.21 (m, 1H), 7.65 (dd, 1H, J$_1$ = 8.6 Hz, J$_2$ = 2.3 Hz), 7.69 (d, 1H, J = 2.2Hz). | +++ |
| 28 | 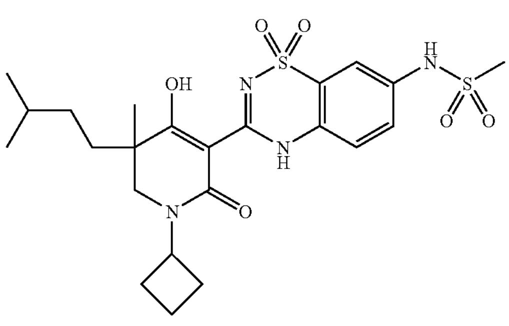 | Prepared as described in Example 2.<br>$^1$H NMR (400 MHz, CDCl$_3$) δ: 0.91 (d, 6H, J = 6.1 Hz), 1.13-1.26 (m, 5H), 1.47-1.56 (m, 2H), 1.60-1.64 (m, 1H), 1.73-1.85 (m, 2H), 2.08-2.32 (m, 4H), 3.05 (s, 3H), 3.12-3.22 (m, 1H), 3.30-3.39 (m, 1H), 4.93-5.02 (m, 1H), 7.11 (bs, 1H), 7.17-7.21 (m, 1H), 7.63-7.65 (m, 1H), 7.69 (bs, 1H). | +++ |

TABLE 1-continued

| Example | Structure | Spectral data | NS5B Polymerase IC50 |
|---|---|---|---|
| 29 | 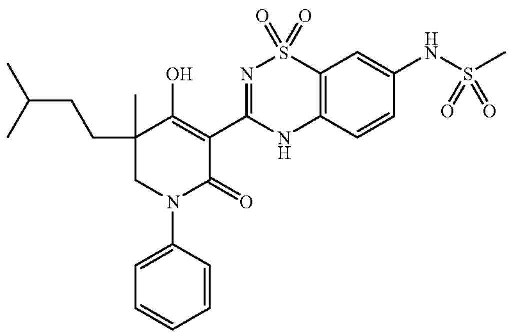 | Prepared as described in Example 2.<br>$^1$H NMR (400 MHz, CDCl$_3$) δ: 0.93 (d, 6H, J = 6.4 Hz), 1.18-1.29 (m, 2H), 1.35 (s, 3H), 1.50-1.61 (m, 1H), 1.77-1.81 (m, 2H), 3.05 (s, 3H), 3.66 (s, 2H), 7.03 (bs, 1H), 7.12-7.14 (m, 1H), 7.28 (bs, 2H), 7.34-7.40 (m, 1H), 7.47-7.51 (m, 2H), 7.58-7.61 (m, 1H), 7.69 (s, 1H), 7.69 (bs, 1H), 13.92 (s, 1H), 13.92 (bs, 1H). | + |
| 30 | 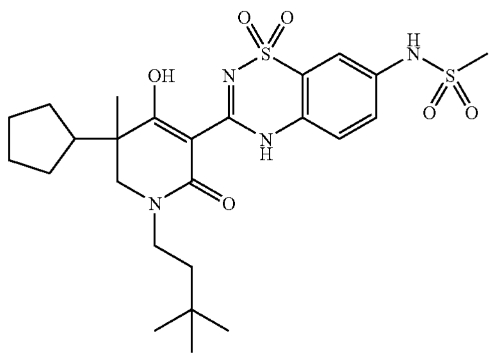 | Prepared as described in Example 2.<br>$^1$H NMR (400 MHz, CDCl$_3$) δ: 1.00 (s, 9H), 1.21 (s, 3H), 1.34-1.75 (m, 10H), 2.18-2.31 (m, 1H), 3.06 (s, 3H), 3.21-3.62 (m, 4H), 6.90 (d, 1H, J = 15.7 Hz), 7.18-7.26 (m, 1H), 7.62-7.69 (m, 2H). | +++ |
| 31 | 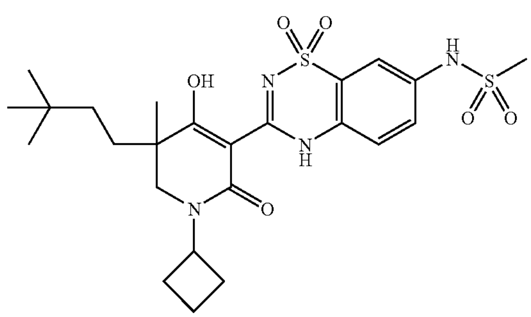 | Prepared as described in Example 2.<br>$^1$H NMR (400 MHz, CDCl$_3$) δ: 0.90 (s, 9H), 1.15-1.27 (m, 5H), 1.49-1.67 (m, 2H), 1.73-1.85 (m, 2H), 2.10-2.31 (m, 4H), 3.05 (s, 3H), 3.13 (d, 1H, J = 12.8 Hz), 3.32 (d, 1H, J = 13.3 Hz), 4.97 (quintet, 1H, J = 8.8 Hz), 7.12 (bs, 1H), 7.18-7.21 (m, 1H), 7.62-7.66 (m, 1H), 7.68-7.70 (m, 1H). | +++ |
| 32 | 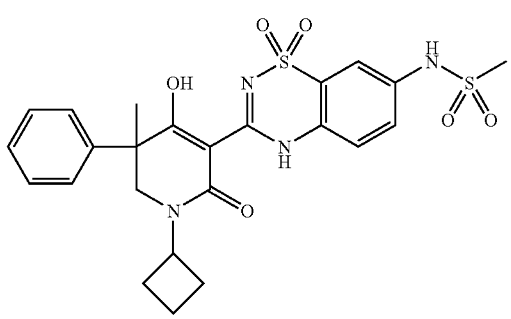 | Prepared as described in Example 2.<br>$^1$H NMR (400 MHz, CDCl$_3$) δ: 1.61 (d, 3H, J = 42.2 Hz), 1.62 (bs, 1H), 1.69-2.31 (m, 6H), 3.05 (d, 3H, J = 5.7 Hz), 3.46-3.50 (m, 1H), 3.82 (dd, 1H, J$_1$ = 46.4 Hz, J$_2$ = 13.3 Hz), 4.61-4.86 (m, 1H), 7.08 (d, 1H, J = 17.8 Hz), 7.19-7.24 (m, 1H), 7.28-7.31 (m, 2H), 7.34-7.38 (m, 2H), 7.63-7.66 (m, 1H), 7.69-7.71 (m, 1H). | + |

TABLE 1-continued

| Example | Structure | Spectral data | NS5B Polymerase IC50 |
|---|---|---|---|
| 33 | 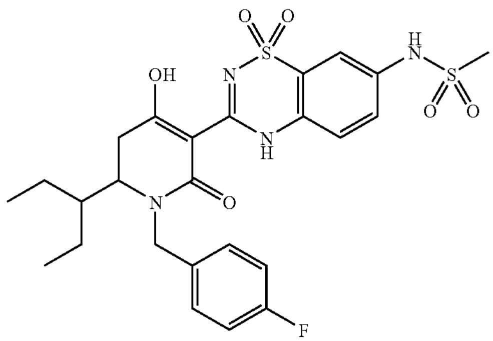 | Prepared as described in Example 4. $^1$H NMR (400 MHz, DMSO-$d_6$) δ: 0.76-0.85 (m, 6H), 1.00-1.08 (m, 1H), 1.15-1.26 (m, 2H), 1.39-1.50 (m, 2H), 1.61 (m, 1H), 3.21 (m, 1H), 3.50-3.64 (m, 2H), 4.26 (m, 1H), 5.10 (d, 1H, J = 15.6 Hz), 7.14-7.18 (m, 2H), 7.37-7.41 (q, 2H, J = 5.6, 8.8 Hz), 7.48-7.52 (dd, 1H, J = 8.8, 2.4 Hz), 7.57 (d, 2H, J = 2.4 Hz), 10.17 (s, 1H), 13.58 (s, 1H). | +++ |
| 34 | 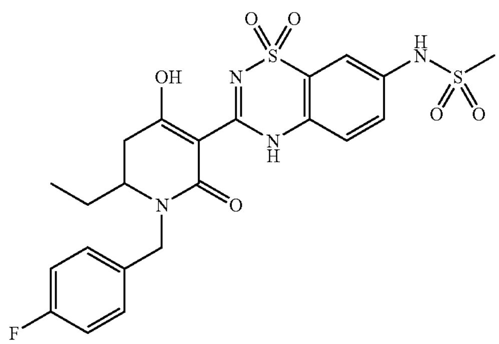 | Prepared as described in Example 4. $^1$H NMR (400 MHz, DMSO-$d_6$) δ: 0.85 (t, 3H, J = 7.6 Hz), 1.61 (m, 2H), 2.57 (m, 1H), 3.05 (s, 3H), 3.20 (1H, m), 3.55 (m, 1H), 4.23 (m, 1H), 5.06 (d, 1H, J = 15.2 Hz), 7.15 (m, 2H), 7.39 (m, 2H), 7.49 (m, 1H), 7.55 (m, 2H), 10.16 (s, 1H), 13.58 (s, 1H). | +++ |
| 35 | 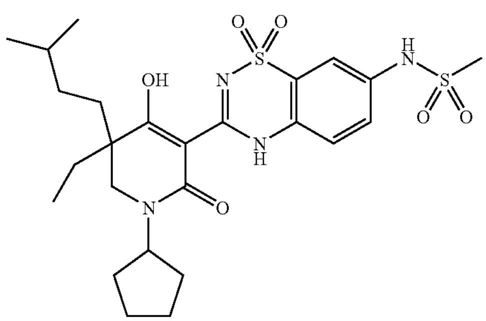 | Prepared as described in Example 2. $^1$H NMR (400 MHz, DMSO-$d_6$) δ: 0.76-0.92 (9H, m), 1.10 1.20 (1H, m), 1.44-1.81 (14H, m), 3.05 (3H, s), 4.70-5.00 (1H, m), 7.45-7.65 (3H, m), 10.10-10.25 (1H, m). | +++ |
| 36 | 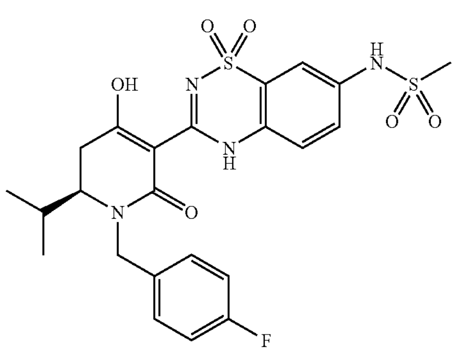 | Prepared as described in Example 4. $^1$H NMR (400 MHz, DMSO-$d_6$) δ: 0.84 (d, 3H, J = 7.2 Hz), 0.94 (d, 3H, J = 7.2 Hz), 2.07 (m, 1H), 2.62 (m, 1H), 3.05 (s, 3H), 3.22 (m, 1H), 3.49 (m, 1H), 4.23 (m, 1H), 5.14 (d, 1H, J = 15.6 Hz), 7.14 (m, 2H), 7.38 (m, 2H), 7.49 (dd, 1H, J = 8.8, 2.4 Hz), 7.56 (m, 2H), 10.16 (s, 1H), 13.52 (s, 1H). | +++ |

TABLE 1-continued

| Example | Structure | Spectral data | NS5B Polymerase IC50 |
|---|---|---|---|
| 37 | 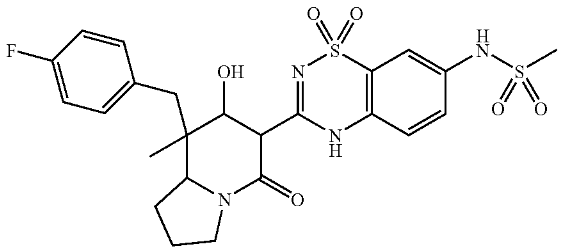 | Prepared as described in Example 5. $^1$H NMR (400 MHz, CD$_2$Cl$_2$) δ: 1.12-1.28 (4H, m), 1.75-2.31 (6H, m), 2.41-2.95 (2H, m), 3.05 (3H, s), 3.35-4.12 (4H, m), 6.85-7.68 (7H, m). | ++ |
| 38 | 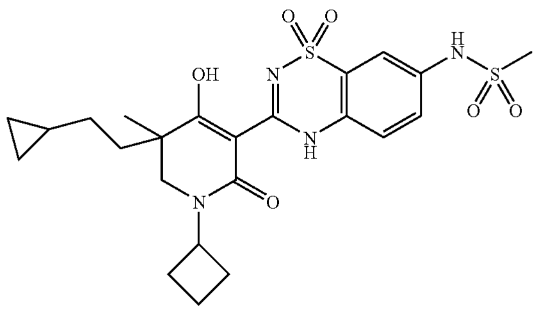 | Prepared as described in Example 2. $^1$H NMR (400 MHz, CDCl$_3$) δ: 0.00-0.05 (2H, m), 0.42-0.46 (2H, m), 0.58-0.66 (1H, m), 1.13-1.25 (5H, m), 1.67-1.84 (4H, m), 2.08-2.28 (4H, m), 3.04 (3H, s), 3.12-3.36 (2H, m), 4.72-5.01 (1H, m), 7.15-7.27 (3H, m), 7.61-7.65 (1H, m), 7.68-7.70 (1H, m). | +++ |
| 39 | 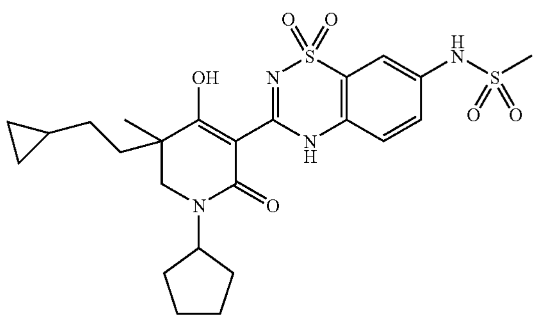 | Prepared as described in Example 2. $^1$H NMR (400 MHz, CDCl$_3$) δ: 0.01-0.06 (2H, m), 0.42-0.47 (2H, m), 0.58-0.67 (1H, m), 1.13-1.27 (5H, m), 1.48-1.80 (10H, m), 2.92-3.22 (5H, m), 4.85-5.04 (1H, m), 7.16-7.20 (1H, m), 7.63-7.67 (2H, m), 7.71-7.73 (1H, m). | ++ |
| 40 | 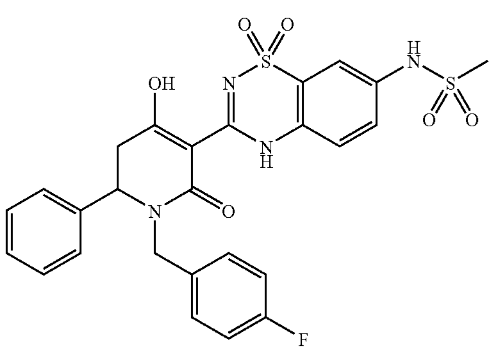 | Prepared as described in Example 4. $^1$H NMR (400 MHz, DMSO-d$_6$) δ: 2.78 (d, 1H, J = 12.0 Hz), 3.06 (s, 3H), 3.61 (m, 1H), 3.90 (d, 1H, J = 14.8 Hz), 4.92 (d, 1H, J = 6.4 Hz), 5.22 (d, 1H, J = 15.2 Hz), 7.13 (m, 2H), 7.23-7.39 (m, 7H), 7.52 (dd, 1H, J = 8.8, 2.4 Hz), 7.57 (d, 1H, J = 2.4 Hz), 7.60 (d, 1H, J = 8.8 Hz), 10.18 (s, 1H), 13.50 (s, 1H). | ++ |

TABLE 1-continued

| Example | Structure | Spectral data | NS5B Polymerase IC50 |
|---|---|---|---|
| 41 | 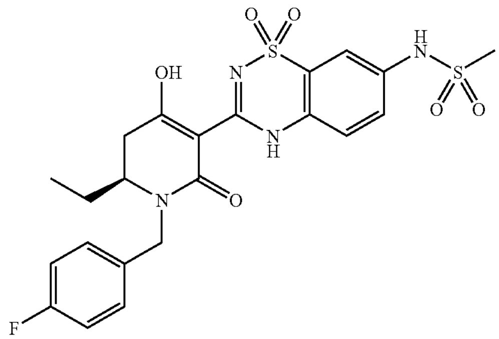 | Prepared as described in Example 4. $^1$HNMR(400MHz,DMSO-d$_6$)δ:0.85(t,3H,J=7.6Hz),1.57-1.68(m,2H),2.55(d,1H,J=17.6Hz),3.05(s,3H),3.20(m,1H),3.55(m,1H),4.23(d,1H,J=12.8Hz),5.06(d,1H,J=14.8Hz),7.15(m,2H),7.39(m,2H),7.49(dd,1H,J=9.2,2.4Hz),7.56(m,2H),10.16(s,1H),13.57(s,1H);ee>98%[HPLC-analysis:ChiralpakAS-RH4.6×250mm,5 micron,0.8mL/min,310nm]. | +++ |
| 42 | 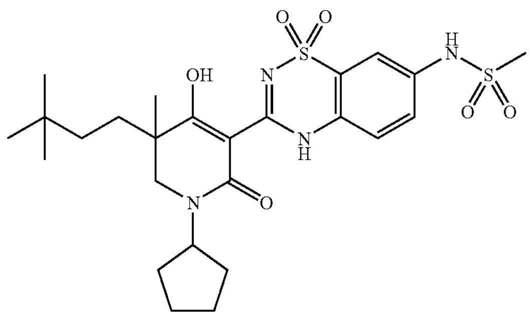 | Prepared as described in Example 2. $^1$H NMR (400 MHz, CDCl$_3$) δ: 0.91 (9H, s), 1.14-1.23 (5H, m), 1.49-1.98 (10H, m), 3.05-3.28 (5H, m), 4.84-5.04 (1H, m), 7.10 (1H, d, J = 12.3 Hz), 7.18-7.21 (1H, m), 7.62-7.66 (1H, m), 7.69-7.70 (1H, m). | ++ |
| 43 | 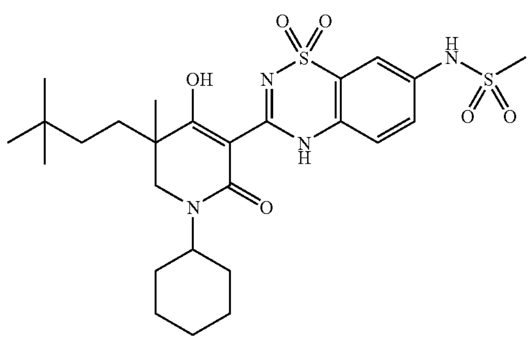 | Prepared as described in Example 2. $^1$H NMR (400 MHz, CDCl$_3$) δ: 0.90 (9H, s), 1.13-1.93 (20H, m), 3.06 (3H, s), 3.09-3.35 (2H, m), 4.36-4.54 (1H, m), 7.03-7.05 (1H, m), 7.18-7.22 (1H, m), 7.62-7.66 (1H, m), 7.68-7.70 (1H, m). | ++ |
| 44 | 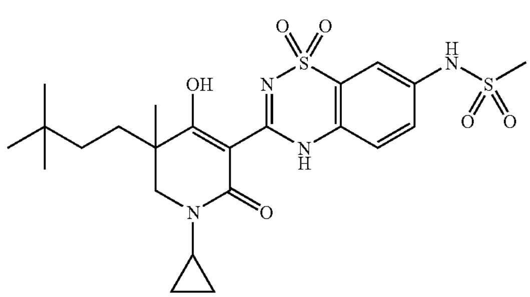 | Prepared as described in Example 2. $^1$H NMR (400 MHz, CDCl$_3$) δ: 1.21-2.15 (20H, m), 3.22-3.92 (6H, m), 7.68-7.76 (1H, m), 7.82-7.85 (1H, m), 8.15-8.17 (1H, m), 8.22 (1H, s). | ++ |

TABLE 1-continued

| Example | Structure | Spectral data | NS5B Polymerase IC50 |
|---|---|---|---|
| 45 | 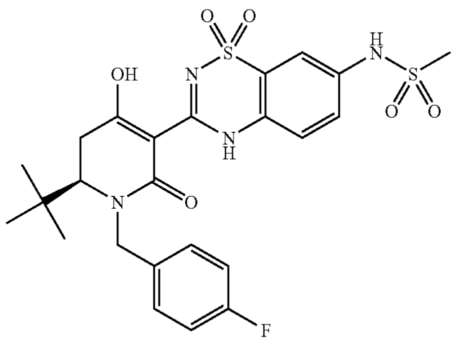 | Prepared as described in Example 4.<br>¹H NMR (400 MHz, DMSO-d₆) δ: 0.96 (s, 9H), 2.70 (d, 1H, J = 18 Hz), 3.04 (s, 3H), 3.56 (d, 1H, J = 6 Hz), 4.17 (d, 1H, J = 14.0 Hz), 5.23 (d, 1H, J = 14.8 Hz), 7.15 (m, 2H), 7.34-7.38 (dd, 2H, J = 8.8, 2.4 Hz), 7.48-7.51 (dd, 1H, J = 9.6, 2.4 Hz), 7.55 (m, 2H), 10.14 (s, 1H), 13.34 (s, 1H). | +++ |
| 46 | 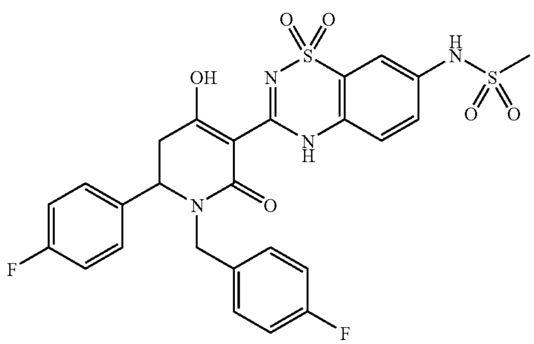 | Prepared as described in Example 4.<br>¹H NMR (400 MHz, DMSO-d₆) δ: 2.76 (m, 1H), 3.05 (s, 3H), 3.59 (dd, 1H, J = 17.6, 6.8 Hz), 3.92 (d, 1H, J = 14.8 Hz), 4.93 (d, 1H, J = 6.8 Hz), 5.16 (d, 1H, J = 17.2 Hz), 7.10-7.19 (m, 4H), 7.29 (m, 2H), 7.35 (m, 2H), 7.52 (dd, 1H, J = 8.8, 2.4 Hz), 7.56 (d, 1H, J = 2.4 Hz), 7.60 (d, 1H, J = 8.8 Hz), 10.18 (s, 1H), 13.47 (s, 1H). | +++ |
| 47 | 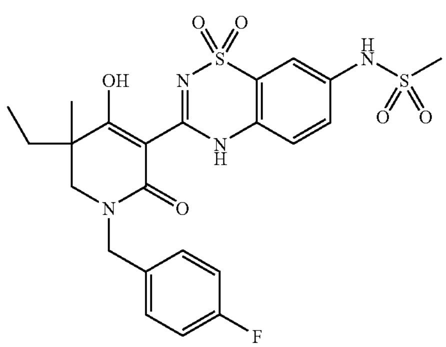 | Prepared as described in Example 2.<br>¹H NMR (400 MHz, CDCl₃) δ: 0.78 (t, 3H, J = 7.4 Hz), 1.04 (s, 1H), 1.14 (s, 3H), 1.27 (s, 1H), 1.50-1.65 (m, 2H), 3.07 (s, 3H), 3.10-3.27 (m, 2H), 4.63 (dd, 2H, J₁ = 59.3 Hz, J₂ = 14.1 Hz), 6.87-6.91 (m, 1H), 7.04-7.08 (m, 2H), 7.24-7.34 (m, 2H), 7.61-7.70 (m, 2H). | +++ |
| 48 | 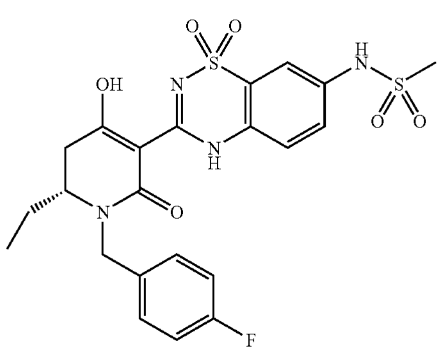 | Prepared as described in Example 4.<br>¹H NMR (400 MHz, DMSO-d₆) δ: 0.83-0.87 (d, 3H, J = 8.0 Hz), 1.67-1.69 (m, 2H), 2.60 (d, 1H, J = 17.6 Hz), 3.09 (s, 3H), 3.19 (d, 1H, J = 13.6 Hz), 3.55 (m, 1H), 4.25 (d, 1H, J = 13.6 Hz), 5.05 (d, 1H, J = 13.2 Hz), 7.15 (m, 2H, J = 9.6 Hz), 7.37-7.41 (m, 2H), 7.48-7.51 (dd, 1H, J = 9.6, 2.4 Hz), 7.57 (d, 1H, J = 2.4 Hz), 10.17 (s, 1H), 13.57 (s, 1H). | +++ |

TABLE 1-continued

| Example | Structure | Spectral data | NS5B Polymerase IC50 |
|---|---|---|---|
| 49 | 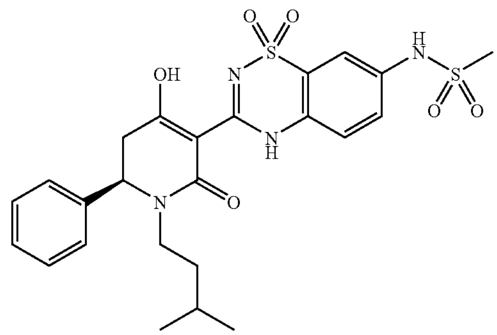 | Prepared as described in Example 4.<br>¹H NMR (400 MHz, DMSO-d₆) δ: 0.85 (d, 3H, J = 7.2 Hz), 0.87 (d, 3H, J = 7.2 Hz), 1.40-1.60 (m, 3H), 3.05 (s, 3H), 2.76 (d, 2H, J = 17.6 Hz), 3.05 (s, 3H), 3.56 (broad s, 1H), 3.95 (m, 1H), 5.00 (d, 1H, J = 5.6 Hz), 7.23-7.38 (m, 5H), 7.51 (m, 1H), 7.56-7.62 (m, 2H), 10.16 (s, 1H), 13.67 (s, 1H). | ++ |
| 50 | 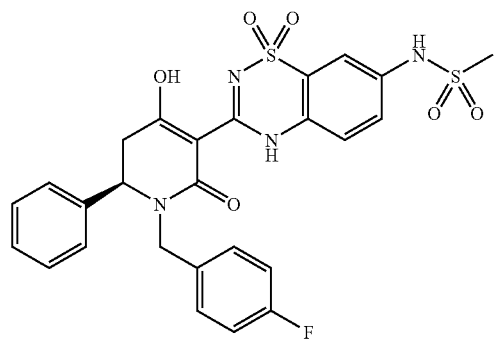 | Prepared as described in Example 4.<br>¹H NMR (400 MHz, DMSO-d₆) δ: 2.78 (d, 1H, J = 17.2 Hz), 3.06 (s, 3H), 3.61 (dd, 1H, J = 16.8, 6.8 Hz), 3.90 (d, 1H, J = 15.2 Hz), 4.92 (d, 1H, J = 6.4 Hz), 5.22 (d, 1H, J = 15.2 Hz), 7.13 (m, 2H), 7.23-7.39 (m, 7H), 7.51 (dd, 1H, J = 8.4, 2.4 Hz), 7.57 (d, 1H, J = 2.4 Hz), 7.60 (d, 1H, J = 8.4 Hz), 10.18 (s, 1H), 13.50 (s, 1H); ee >97% [HPLC-analysis: Chiralpak AS-RH 4.6 × 250 mm, 5 micron, 0.8 mL/min, 310 nm]. | +++ |
| 51 | 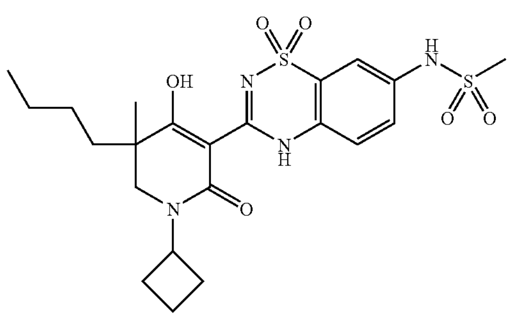 | Prepared as described in Example 2.<br>¹H NMR (400 MHz, CD₂Cl₂) δ: 0.91-0.96 (m, 3H), 1.16 (s, 1H), 1.27 (s, 3H), 1.32-1.37 (m, 2H), 1.48-1.69 (m, 4H), 1.76-1.85 (m, 2H), 2.13-2.31 (m, 4H), 3.07 (s, 3H), 3.16-3.42 (m, 2H), 4.99 (quintet, 1H, J = 8.8 Hz), 6.82 (bs, 1H), 7.24-7.28 (m, 1H), 7.54-7.58 (m, 1H), 7.65-7.68 (m, 1H), 14.37 (bs, 1H). | +++ |
| 52 | 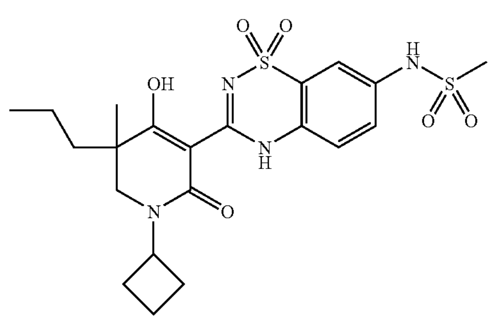 | Prepared as described in Example 2.<br>¹H NMR (400 MHz, CD₂Cl₂) δ: 0.81-0.86 (m, 3H), 1.05 (s, 1H), 1.16 (s, 3H), 1.22-1.32 (m, 2H), 1.40-1.49 (m, 2H), 1.63-1.73 (m, 2H), 2.01-2.20 (m, 4H), 2.95 (s, 3H), 3.05-3.33 (m, 2H), 4.88 (quintet, 1H, J = 8.8 Hz), 6.68 (bs, 1H), 7.12-7.16 (m, 1H), 7.42-7.47 (m, 1H), 7.54-7.56 (m, 1H), 14.25 (bs, 1H). | +++ |

TABLE 1-continued

| Example | Structure | Spectral data | NS5B Polymerase IC50 |
|---|---|---|---|
| 53 | 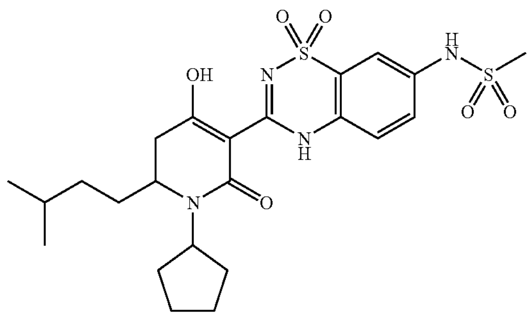 | Prepared as described in Example 4. <sup>1</sup>H NMR (400 MHz, CDCl<sub>3</sub>) δ: 0.91 (3H, s), 0.92 (3H, s), 1.09-1.27 (3H, m), 1.50-2.06 (10H, m), 2.55-2.67 (1H, m), 2.95-3.01 (1H, m), 3.06 (3H, s), 3.41-3.45 (1H, m), 4.52-4.60 (1H, m), 7.17-7.21 (1H, m), 7.62-7.67 (1H, m), 7.70-7.71 (1H, m). | + |
| 54 | 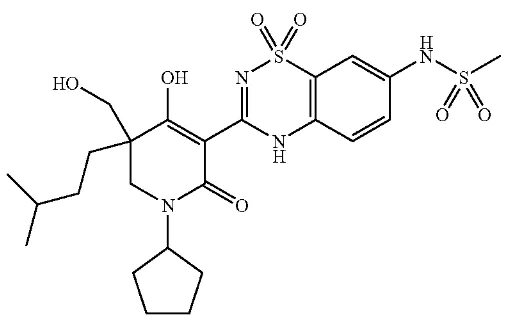 | Prepared as described in Example 2. $^1$H NMR (400 MHz, DMSO-$d_6$) δ: 0.89-0.97 (6H, m), 1.12-1.30 (1H, m), 1.35-2.05 (12H, m), 3.07 (3H, d, J = 7.2 Hz), 3.12-3.23 (1H, m), 3.50-3.50 (2H, m), 3.94-4.14 (2H, m), 6.58 (1H, d, J = 15.6 Hz), 7.21 (1H, t, J = 8.0 Hz), 7.58-7.66 (1H, m). | +++ |
| 55 | 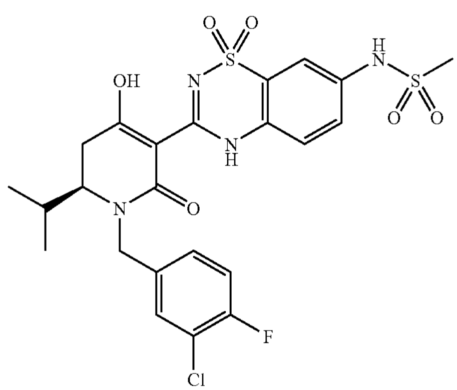 | Prepared as described in Example 4. $^1$H NMR (400 MHz, DMSO-$d_6$) δ: 0.85 (d, 3H, J = 6.4 Hz), 0.94 (d, 3H, J = 6.8 Hz), 2.07 (m, 1H), 2.61 (d, 1H, J = 17.6 Hz), 3.05 (s, 3H), 3.25 (m, 1H), 3.53 (m, 1H), 4.23 (d, 1H, J = 15.2 Hz), 5.11 (d, 1H, J = 15.2 Hz), 7.34 (m, 2H), 7.49 (dd, 1H, J = 8.8, 2.4 Hz), 7.56 (m, 3H), 10.16 (s, 1H), 13.45 (s, 1H). | +++ |
| 56 | 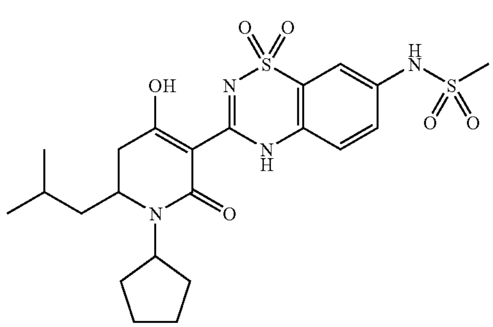 | Prepared as described in Example 4. $^1$H NMR (400 MHz, DMSO-$d_6$) δ: 0.88-0.93 (6H, m), 1.19-1.29 (1H, m), 1.49-1.62 (3H, m), 1.68-1.93 (7H, m), 3.05 (3H, s), 3.69-3.81 (1H, m), 4.43-4.47 (1H, m), 7.49-7.57 (1H, m), 10.15 (1H, s), 13.66 (1H, bs). | + |

TABLE 1-continued

| Example | Structure | Spectral data | NS5B Polymerase IC50 |
|---|---|---|---|
| 57 | 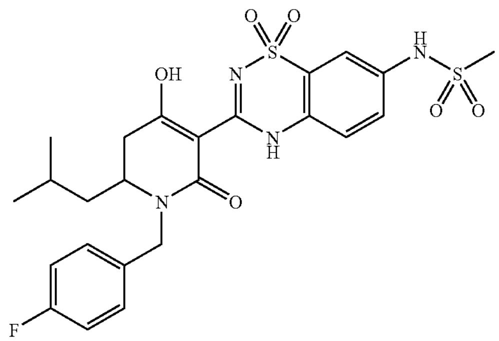 | Prepared as described in Example 4.<br>$^1$H NMR (400 MHz, DMSO-d$_6$) δ: 0.84 (6H, dd, J$_1$ = 22.5 Hz, J$_2$ = 6.2 Hz), 1.31-1.38 (1H, m), 1.52-1.61 (2H, m), 3.06 (3H, s), 3.18-3.27 (1H, m), 3.59-3.63 (1H, m), 4.17-4.25 (1H, m), 5.07 (1H, d, J = 15.4 Hz), 7.15-7.19 (2H, m), 7.38-7.42 (2H, m), 7.50-7.52 (1H, m), 7.56-7.58 (2H, m), 10.17 (1H, s), 13.57 (1H, s). | +++ |
| 58 | 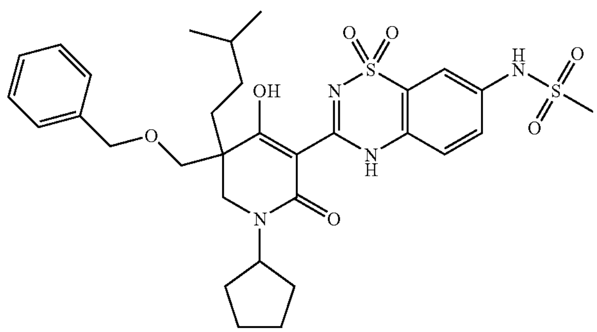 | Prepared as described in Example 2.<br>$^1$H NMR (400 MHz, CDCl$_3$) δ: 0.87-0.90 (6H, m), 0.97-1.33 (3H, m), 1.42-1.96 (12H, m), 3.05-3.06 (3H, m), 3.17-3.31 (1H, m), 3.48-3.67 (3H, m), 4.46-4.59 (2H, m), 4.81-5.03 (1H, m), 6.54-6.57 (1H, m), 7.18-7.22 (1H, m), 7.29-7.38 (5H, m), 7.58-7.66 (2H, m). | + |

Biological Testing

The ability of compounds of Formula I to inhibit HCV replication can be demonstrated in the following in vitro assays.

Compounds were tested for HCV polymerase inhibition. Assays were performed in a 96-well streptavidin-coated FlashPlate using 20 nM enzyme, 0.5 μCi of [α-$^{33}$P]GTP, 0.6 μM GTP, and 250 nM 5'biotinylated oligo (rG$_{13}$)/poly rC in 20 mM Tris-HCl, pH 7.5, 5 mM MgCl$_2$, 5 mM dithiothreitol, 0.1 g/L bovine serum albumin, and 100 U/mL RNAse inhibitor. The reaction was stopped by aspiration after 75 min at 28° C. and the plate was washed several times. After washing and drying the plate, incorporated radioactivity was counted using a Microbeta scintillation counter. IC$_{50}$ values were calculated relative to the uninhibited control and inhibition data were fitted to a 4-parameter IC$_{50}$ equation. For very potent inhibitors, the data were fitted to a tight binding quadratic equation to obtain IC$_{50}$ values.

Test results (IC$_{50}$ values) for compounds of Formula I are summarized in Table 1, wherein +++ means NS5B polymerase inhibition with IC$_{50}$ values less than 0.10 μM, ++ means IC$_{50}$ values between 0.10 μM and 1 μM, and + means IC$_{50}$ values between 1 μM and 4 μM.

HCV Replicon Assay (Replicon EC50 (μM))

The cell culture component of the assay is performed essentially as described by Bartenschlager et al., *Hepatology*, 35, 694-703 (2002), wherein exponentially growing HCV Huh-7/C24 replicon cells are seeded at 4.5×10$^3$ cells/well in 96 well plates and 24 hours later are treated with six point half-log concentration of compound. After 72 hours exposure the media is discarded from the compound assay plate and the cell monolayers are lysed by addition of 150 μl lysis mixture (Genospectra) with incubation at 53° C. for 45 minutes. Following incubation, each lysate is thoroughly mixed and 5 μl (NS3 probe) or 10 μl (GAPDH probe) of each lysate is then transferred to the capture plate and analyzed by bDNA assay.

Branched DNA (bDNA) Assay

Based on provided sequences for NS3 [AJ242652], Genospectra (Fremont, Calif., USA) designed and synthesized probes to these analytes (together with GAPDH). Cellular bDNA analysis is carried out essentially as described in the Genospectra protocol (details in Shyamala, V. et al, *Anal Biochem*, 266, 140-7 (1999)), wherein target specific capture extenders, label extenders and blocking probes are added to the capture plate after the addition of 5 or 10 μl cell lysate. After annealing overnight, during which the target RNA is captured to the plate via interaction with the capture extenders, the plate is washed, and then amplifier (which binds via the label extenders) and label probe are sequentially added.

After subsequent addition of the chemilumigenic substrate (dioxetan), each plate is read by luminometer (Wallac 1420 Multilabel HTS Counter Victor 2). The luminescence signal is proportional to the amount of mRNA present in each lysate. In addition to the samples, cell lysate only (no probe) background controls are also included on each bDNA assay plate and the average signal from these control wells is subtracted from the sample reading prior to analysis. Percent of no drug control is determined for both the NS3 and GAPDH signals for each compound also. Percent inhibition is determined for each compound concentration in relation to the no drug control to calculate the EC$_{50}$.

It is to be understood that the foregoing description is exemplary and explanatory in nature, and is intended to illustrate the invention and its preferred embodiments. Through

What is claimed is:

1. A compound of Formula I

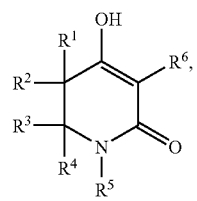

I wherein
$R^1$, $R^2$, $R^3$, and $R^4$ are independently H, halo, cyano, hydroxyl, $C_1$-$C_6$ hydroxyalkyl, $C_1$-$C_6$ alkoxy, amino, $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_2$-$C_6$ alkenyl, $C_2$-$C_6$ alkynyl, aryl, $C_1$-$C_6$ alkylene(aryl), heterocyclyl, or $C_1$-$C_6$ alkylene(heterocyclyl) or $R^1$ and $R^2$ or $R^3$ and $R^4$ can combine with the atom(s) to which they are attached to form a 3- to 6-membered spiro cycloalkyl ring or $R^3$ and $R^5$ or $R^4$ and $R^5$ can combine with the atom(s) to which they are attached to form a 4- to 6-membered heterocyclyl ring,
$R^5$ is H, amino, $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_1$-$C_6$ alkylene(aryl), $C_1$-$C_6$ alkylene(heterocyclyl), aryl, or heterocyclyl,
$R^6$ is

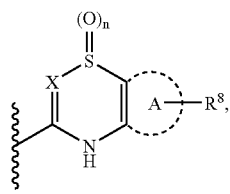

wherein n is 2,
X is N,
and
Ring A is a 5- or 6-membered aryl, optionally substituted by 1-3 $R^8$ moieties,
$R^8$ is H, halo, nitro, —$CHR^9S(O)_2R^{10}$, —$NR^{10}R^{11}$, —$NR^9S(O)_2R^{10}S$ or $NR^9S(O)_2NR^{10}R^{11}$, wherein $R^9$, $R^{10}$, and $R^{11}$ are independently H, $C_1$-$C_6$ alkyl, $C_3$-$C_8$ cycloalkyl, aryl, or heterocyclyl, or $R^9$ and $R^{10}$ or $R^{10}$ and $R^{11}$ combine with the atom(s) to which they are attached to form a 5- or 6-membered heterocyclyl ring,
wherein the above alkyl, alkenyl, alkynyl, aryl, cycloalkyl, or heterocyclyl moieties provided in $R^1$, $R^2$, $R^3$, $R^4$, $R^5$, $R^9$, $R^{10}$, and $R^{11}$ are each optionally and independently substituted by 1-3 substituents selected from
alkoxy,
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
oxo,
—C(O)OH, —C(O)$_2$($C_1$-$C_6$ alkyl), —C(O)$_2$($C_3$-$C_8$ cycloalkyl), —C(O)$_2$(aryl), —C(O)$_2$(heterocyclyl), —C(O)$_2$($C_1$-$C_6$ alkylene)aryl, —C(O)$_2$($C_1$-$C_6$ alkylene)heterocyclyl, —C(O)$_2$($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl,
wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt, tautomer or stereoisomer thereof.

2. The compound of claim 1, wherein $R^1$, $R^2$, $R^3$, and $R^4$ are independently H, halo, cyano, $C_1$-$C_6$ hydroxyalkyl, $C_1$-$C_6$ alkoxy, $C_1$-$C_6$ alkyl, $C_3$-$C_8$ cycloalkyl, $C_1$-$C_6$ alkylene(cycloalkyl), $C_2$-$C_6$ alkenyl, $C_2$-$C_6$ alkynyl, aryl, $C_1$-$C_6$ alkylene (aryl), heterocyclyl, or $C_1$-$C_6$ alkylene(heterocyclyl) or $R^1$ and $R^2$ or $R^3$ and $R^4$ can combine with the atom(s) to which they are attached to form a 3- to 6-membered spiro cycloalkyl ring, or $R^3$ and $R^5$ or $R^4$ and $R^5$ can combine with the atom(s) to which they are attached to form a 4- to 6-membered heterocyclyl ring.

3. The compound of claim 2, wherein $R^1$, $R^2$, $R^3$, and $R^4$ are independently selected from

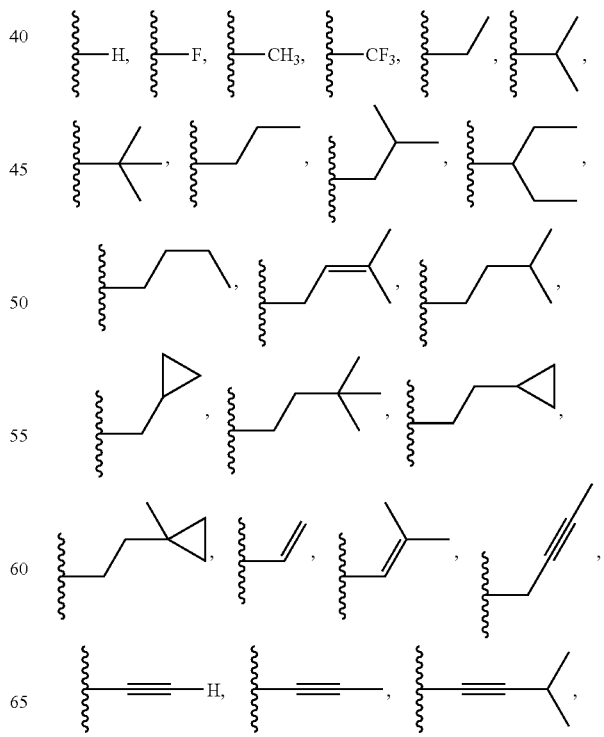

-continued

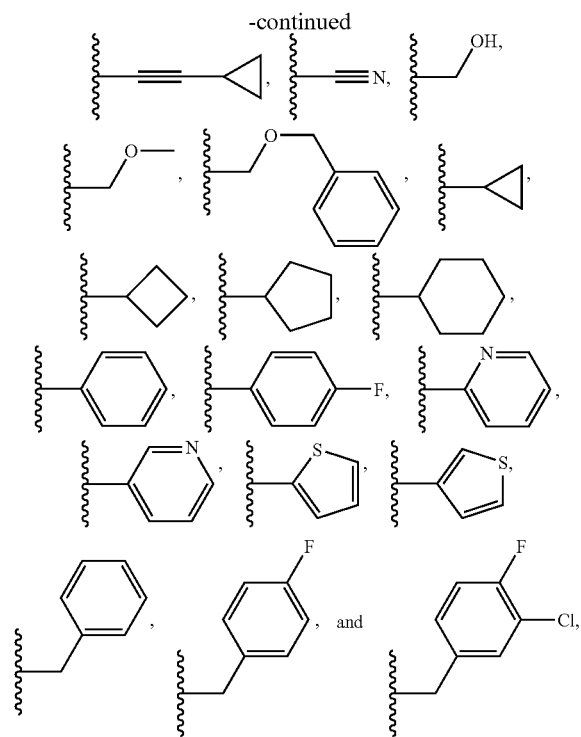

or R¹ and R² or R³ and R⁴ can combine with the atom(s) to which they are attached to form spiro rings from

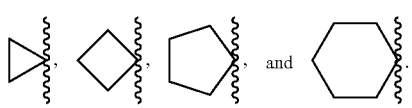

4. The compound of claim 3, wherein R¹, R², R³, and R⁴ are independently selected from

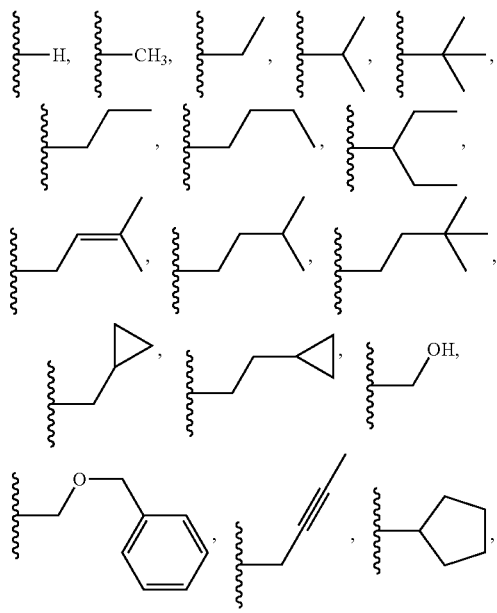

-continued

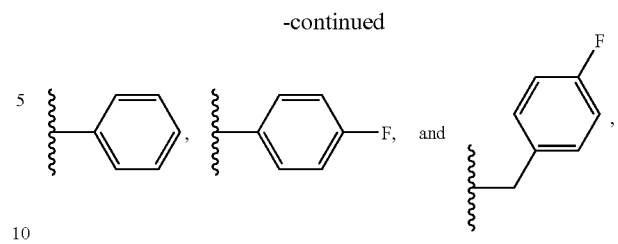

or R¹ and R² or R³ and R⁴ can combine with the atom(s) to which they are attached to form spiro rings selected from

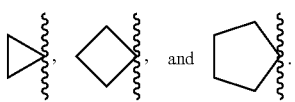

5. The compound of claim 1, wherein $R^5$ is $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_1$-$C_6$ alkylene(aryl), aryl, or heterocyclyl.

6. The compound of claim 5, wherein $R^5$ is selected from

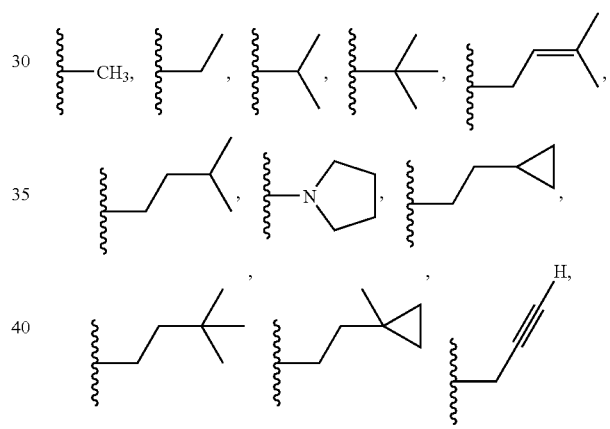

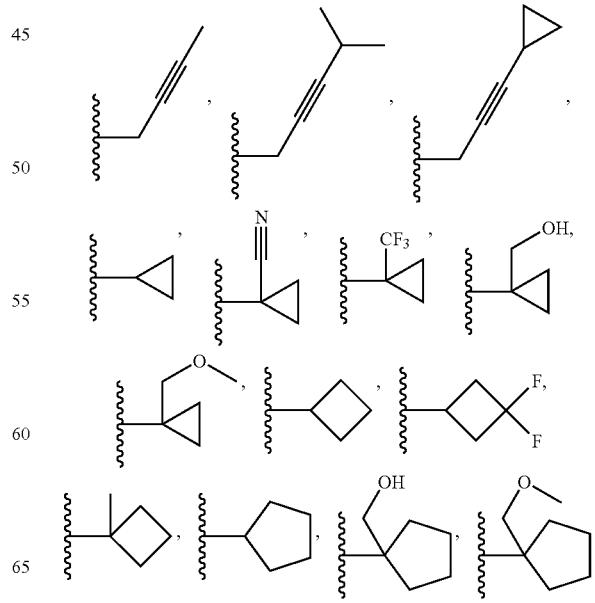

-continued

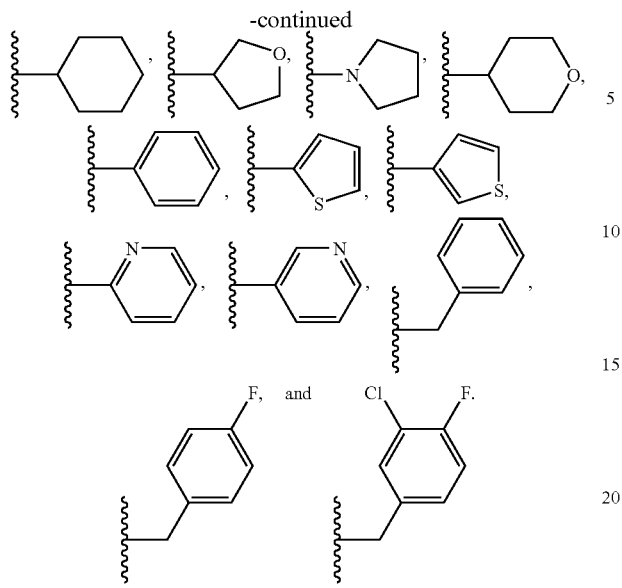

7. The compound of claim 6, wherein R⁵ is selected from

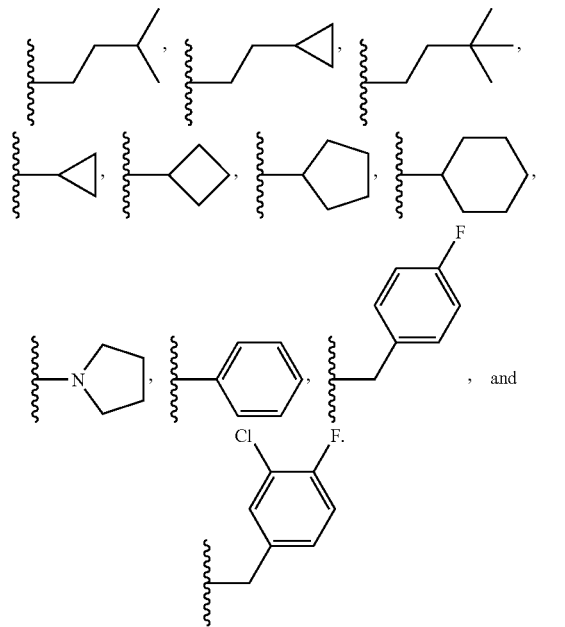

8. The compound of claim 1, wherein R³ and R⁵ or R⁴ and R⁵ combine to form a 4- to 6-membered heterocyclyl ring.

9. The compound of claim 1, wherein R⁶ is

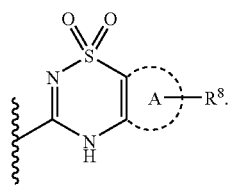

10. The compound of claim 1, wherein Ring A is

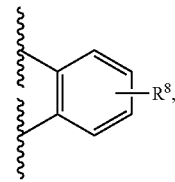

wherein R⁸ is —CHR⁹S(O)₂R¹⁰, —NR¹⁰R¹¹, —NR⁹S(O)₂R¹⁰, or NR⁹S(O)₂NR¹⁰R¹¹, wherein R⁹, R¹⁰, and R¹¹ are independently H, C₁-C₆ alkyl, C₃-C₈ cycloalkyl, aryl, or heterocyclyl, or R⁹ and R¹⁰ or R¹⁰ and R¹¹ combine with the atom(s) to which they are attached to form a 5- or 6-membered heterocyclyl ring.

11. The compound of claim 1, wherein R⁸ is selected from

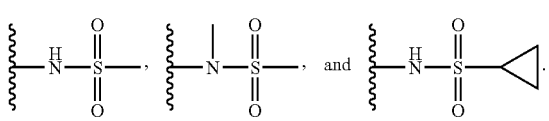

12. The compound of claim 11, wherein R⁸ is

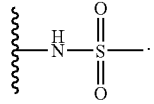

13. A compound selected from

N-{3-[1-(4-Fluoro-benzyl)-4-hydroxy-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[4-Hydroxy-5-methyl-1,5-bis-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[5-(4-Fluoro-benzyl)-8-hydroxy-6-oxo-5-aza-spiro[2,5]oct-7-en-7-yl]-1,1-dioxo-1,4-dihydro-1λ⁶-benzo[1,2,4]thiadiazin-7-yl}-methanesulfonamide, N-{3-[6-(4-Fluoro-benzyl)-9-hydroxy-7-oxo-6-aza-spiro[4,5]dec-8-en-8-yl]-1,1-dioxo-1,4-dihydro-1λ⁶-benzo[1,2,4]thiadiazin-7-yl}-methanesulfonamide, N-{3-[5-Hydroxy-8-methyl-8-(3-methyl-butyl)-7-oxo-1,2,3,7,8,8a-hexahydro-indolizin-6-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-6-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[4-Hydroxy-5-methyl-5-(3-methyl-butyl)-2-oxo-1-pyrrolidin-1-yl-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-5-methyl-5-(3-methyl-butyl)-2-oxo-1,2,5,6-tetrahydro-pyridin-3-yl]-1,1-dioxo-1,4-dihydro-1λ⁶-benzo[1,2,4]thiadiazin-7-yl}-methanesulfonamide, N-{3-[1-(4-Fluoro-benzyl)-4-hydroxy-5-(3-methyl-but-2-enyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-5,5-dimethyl-1-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[7-(4-Fluoro-benzyl)-10-hydroxy-8-oxo-7-azaspiro[4,5]dec-9-en-9-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-5,5-dimethyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1,5-Bis-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-5-methyl-2-oxo-5-phenyl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-5-(4-fluoro-benzyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-[3-(1-Cyclopentyl-4-hydroxy-5,5-dimethyl-2-oxo-1,2,5,6-tetrahydro-pyridin-3-yl)-1,1-dioxo-1,4-dihydro-1$\lambda^6$-benzo[1,2,4]thiadiazin-7-yl]-methanesulfonamide, N-{3-[1-Cyclohexyl-5-(4-fluoro-benzyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopropyl-5-(4-fluoro-benzyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-4-hydroxy-5-(3-methyl-but-2-enyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-4-hydroxy-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[6-(4-Fluoro-benzyl)-9-hydroxy-7-oxo-6-aza-spiro[3,5]non-8-en-8-yl]-1,1-dioxo-1,4-dihydro-1$\lambda^6$-benzo[1,2,4]thiadiazin-7-yl}-methanesulfonamide, N-{3-[5-Cyclopropylmethyl-1-(4-fluoro-benzyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-[3-(5-But-2-ynyl-1-cyclopentyl-4-hydroxy-5-methyl-2-oxo-1,2,5,6-tetrahydro-pyridin-3-yl)-1,1-dioxo-1,4-dihydro-1$\lambda^6$-benzo[1,2,4]thiadiazin-7-yl]-methanesulfonamide, N-{3-[1-Cyclohexyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclobutyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-5-methyl-5-(3-methyl-butyl)-2-oxo-1-phenyl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[5-Cyclopentyl-1-(3,3-dimethyl-butyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclobutyl-5-(3,3-dimethyl-butyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-[3-(1-Cyclobutyl-4-hydroxy-5-methyl-2-oxo-5-phenyl-1,2,5,6-tetrahydro-pyridin-3-yl)-1,1-dioxo-1,4-dihydro-1$\lambda^6$-benzo[1,2,4]thiadiazin-7-yl]-methanesulfonamide, N-{3-[6-(1-Ethyl-propyl)-1-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[6-Ethyl-1-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-5-ethyl-4-hydroxy-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-6(R)-isopropyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[8-(4-Fluoro-benzyl)-5-hydroxy-8-methyl-7-oxo-1,2,3,7,8,8a-hexahydro-indolizin-6-yl]-1,1-dioxo-1,4-dihydro-1$\lambda^6$-benzo[1,2,4]thiadiazin-7-yl}-methanesulfonamide, N-{3-[1-Cyclobutyl-5-(2-cyclopropyl-ethyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-5-(2-cyclopropyl-ethyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-6-phenyl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[6(R)-Ethyl-1-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-5-(3,3-dimethyl-butyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclohexyl-5-(3,3-dimethyl-butyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopropyl-5-(3,3-dimethyl-butyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[6(R)-tert-Butyl-1-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-6-(4-fluoro-phenyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[5-Ethyl-1-(4-fluoro-benzyl)-4-hydroxy-5-methyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[6(S)-Ethyl-1-(4-fluoro-benzyl)-4-hydroxy-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[4-Hydroxy-1-(3-methyl-butyl)-2-oxo-6(R)-phenyl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-6(R)-phenyl-1,2,5,6-tetrahydro-pyridin-3-yl]-1,1-dioxo-1,4-dihydro-1$\lambda^6$-benzo[1,2,4]thiadiazin-7-yl}-methanesulfonamide, N-[3-(5-Butyl-1-cyclobutyl-4-hydroxy-5-methyl-2-oxo-1,2,5,6-tetrahydro-pyridin-3-yl)-1,1-dioxo-1,4-dihydro-1$\lambda^6$-benzo[1,2,4]thiadiazin-7-yl]-methanesulfonamide, N-[3-(1-Cyclobutyl-4-hydroxy-5-methyl-2-oxo-5-propyl-1,2,5,6-tetrahydro-pyridin-3-yl)-1,1-dioxo-1,4-dihydro-1$\lambda^6$-benzo[1,2,4]thiadiazin-7-yl]-methanesulfonamide, N-{3-[1-Cyclopentyl-4-hydroxy-6-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-Cyclopentyl-4-hydroxy-5-hydroxymethyl-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-{3-[1-(3-Chloro-4-fluoro-benzyl)-4-hydroxy-6(R)-isopropyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide, N-[3-(1-Cyclopentyl-4-hydroxy-6-isobutyl-2-oxo-1,2,5,6-tetrahydro-pyridin-3-yl)-1,1-dioxo-1,4-dihydro-1$\lambda^6$-benzo[1,2,4]thiadiazin-7-yl]-methanesulfonamide, and N-{3-[1-(4-Fluoro-benzyl)-4-hydroxy-6-isobutyl-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide N-{3-[5-Benzyloxymethyl-1-cyclopentyl-4-hydroxy-5-(3-methyl-butyl)-2-oxo-1,2,5,6-tetrahydro-pyridin-3-yl]-1,1-dioxo-1,4-dihydro-1$\lambda^6$-benzo[1,2,4]thiadiazin-7-yl}-methanesulfonamide.

14. A pharmaceutically acceptable composition comprising a compound of claim 1 and a pharmaceutically acceptable carrier.

15. A method for treating hepatitis C virus infection in a mammal in need thereof, comprising administering to the mammal a therapeutically effective amount of a compound of claim 1.

16. The method of claim 15 wherein the mammal is a human.

17. The method of claim 16 further comprising administering an additional therapeutic agent to the mammal.

18. The method of claim 17 wherein the additional therapeutic agent is selected from the group consisting of an antibiotic, an antiemetic agent, an antidepressant, an antifungal agent, an anti-inflammatory agent, an antiviral agent, an anticancer agent, an immunomodulatory agent, an α-interferon, a β-interferon, a ribavirin, an alkylating agent, a hormone, a cytokine and a toll-like receptor modulator.

19. The method of claim 18 wherein the additional therapeutic agent is a toll-like receptor modulator.

* * * * *